(12) United States Patent
Chen et al.

(10) Patent No.: US 9,820,942 B2
(45) Date of Patent: Nov. 21, 2017

(54) LIPIDOSOME PREPARATION, PREPARATION METHOD AND APPLICATION THEREOF

(71) Applicant: BIOMICS BIOTECHNOLOGIES CO.,LTD., Jiangsu (CN)

(72) Inventors: Jianxin Chen, Jiangsu (CN); Wei Peng, Jiangsu (CN); Tiejun Li, Jiangsu (CN); Hui Zhu, Jiangsu (CN); Yan Ni, Jiangsu (CN); Wenjian Feng, Jiangsu (CN)

(73) Assignee: BIOMICS BIOTECHNOLOGIES CO., LTD., Nantong (CN)

( * ) Notice: Subject to any disclaimer, the term of this patent is extended or adjusted under 35 U.S.C. 154(b) by 23 days.

(21) Appl. No.: 14/436,060

(22) PCT Filed: Mar. 6, 2013

(86) PCT No.: PCT/CN2013/072236
§ 371 (c)(1),
(2) Date: Apr. 15, 2015

(87) PCT Pub. No.: WO2014/134797
PCT Pub. Date: Sep. 12, 2014

(65) Prior Publication Data
US 2015/0272886 A1    Oct. 1, 2015

(51) Int. Cl.
*A61K 9/127*  (2006.01)
*A61K 31/713*  (2006.01)
*C12N 15/11*  (2006.01)
*C12N 15/113*  (2010.01)

(52) U.S. Cl.
CPC .......... *A61K 9/1272* (2013.01); *A61K 9/1278* (2013.01); *A61K 31/713* (2013.01); *C12N 15/111* (2013.01); *C12N 15/113* (2013.01); *C12N 2310/14* (2013.01); *C12N 2310/141* (2013.01); *C12N 2310/16* (2013.01); *C12N 2320/32* (2013.01)

(58) Field of Classification Search
CPC combination set(s) only.
See application file for complete search history.

(56) References Cited

U.S. PATENT DOCUMENTS

2003/0229037 A1* 12/2003 Massing .............. C07J 41/0055
                                                    514/44 R
2012/0183602 A1*  7/2012 Chen ................... A61K 9/1272
                                                      424/450

FOREIGN PATENT DOCUMENTS

| CN | 101120921 | 2/2008 |
| CN | 102154265 | 8/2011 |
| CN | 102727436 | 10/2012 |
| CN | 102895190 | 1/2013 |

OTHER PUBLICATIONS

Hung, W. et al. (2007). "The Condensing Effect of Cholesterol in Lipid Bilayers." Biophysical Journal, 92(11): 3960-3967.*
Google Translate of CN102895190.*

* cited by examiner

*Primary Examiner* — Robert A Wax
*Assistant Examiner* — Amanda Boswell
(74) *Attorney, Agent, or Firm* — K&L Gates LLP; Louis C. Cullman; David Diamond

(57) ABSTRACT

The present invention discloses a liposome formulation, its preparation method, and its application in the treatment of diseases caused by abnormal gene expression. The liposome formulation comprises complementary cationic lipid pairs, phospholipids, and long-circulating lipids. The method of preparing the liposome formulation comprises: mixing the complementary cationic lipid pairs with the phospholipid and the long-circulating lipid to generate pre-formed vesicles; and then mixing the pre-formed vesicles with the nucleic acid solution to generate the liposome-nucleic acid formulation. This liposome formulation provided by the present invention is easily prepared; and in the treatment of diseases caused by abnormal gene expression, the liposome formulation can be used to deliver in vivo therapeutic agents, including nucleic acids.

17 Claims, 7 Drawing Sheets

LIPIDOSOME PREPARATION, PREPARATION METHOD AND APPLICATION THEREOF

FIELD OF THE INVENTION

The present invention relates to a therapeutic formulation for in vivo delivery of agents, particularly, a liposome formulation.

BACKGROUND OF THE INVENTION

In recent years, different types of nucleic acid have been studied for treatment of human diseases. The therapeutic nucleic acids are expected to be developed into a new generation of gene therapy, including DNAs, RNAs, their chemically modified structures and mimics. Among them, RNAs include small interfering RNAs (siRNAs), microRNAs (miRNAs), RNA aptamers, small ligand RNAs (sliRNAs), etc; DNAs include plasmids, etc. These nucleic acids act through a variety of mechanisms. For example, siRNAs and miRNAs regulate the expression of intracellular specific genes by means of a process termed RNA interference (RNAi). When siRNAs or miRNAs are introduced into cytoplasm, double-stranded siRNAs or miRNAs bind to specific intracellular proteins to form RNA Inducing Silencing Complex (RISC). After unwinding of siRNAs in RISC, siRNAs recognize and bind to mRNAs by the mechanism of sequence complementary, leading to cleavage of the mRNAs and down-regulation of the gene expression. Therefore, RNAi provides a potential gene therapy, via complementation with target gene and inhibition of the expression of mRNAs encoding proteins.

The applications of RNAi are extremely broad, since siRNAs or miRNAs targeting a certain protein can be de novo chemically synthesized. A large number of researchers have reported that siRNAs can specifically down-regulate target protein in both in vitro and in vivo model systems. To date, dozens of siRNAs drug candidates are under clinical evaluation.

However, two problems currently faced by siRNAs and other potential therapeutic nucleic acids are, the first, low resistance to the degradation of ribonucleases in cytoplasm, the second, limited ability to cross cell membrane, gain access to intracellular compartment, and bind RISC complex, when naked-siRNAs or miRNAs are administered systematically. These nucleic acids can be stabilized by introduction of chemically modified nucleotides, for example, phosphothioate group-modified nucleotides. Nevertheless, these chemical modifications can only provide limited protection from nuclease degradation, and may compromise the activity of the nucleic acids. Intracellular delivery of therapeutic nucleic acids can be facilitated by various carrier systems, such as polymers, cationic liposomes or chemical modification, for example covalent linkage with cholesterol molecules. Even though, there is still a need to further improve the delivery systems, so as to enhance their in vivo stability and transmembrane activity, as well as to reduce the adverse effect of chemical modifications.

In serum or within the cells, the primary issue faced by therapeutic nucleic acids is stability. In the presence of endo-ribonucleases or exonuclease, nucleic acids are readily to be degraded, with a very short half-life (Zelphati O, et al, Antisense. Res. Dev. 1993(3):323-338). This problem has been partially overcome by the introduction of chemical modified nucleotides, for example modifications at the phosphodiester linkage, at the nucleotide base or at the sugar. Although these modifications decrease siRNAs degradation in serum or within the cells, limitation still exists and the stability problem has not been completely solved.

On the other hand, limited activity to penetrate cell membranes is another problem for the development of therapeutic nucleic acids. To improve this situation, liposome-based carrier systems have been employed to facilitate the delivery of chemically modified or unmodified therapeutic nucleic acids. Numerous studies have reported that cationic liposomes can be used to encapsulate siRNAs, thereby forming liposome-nucleic acid formulation. The delivery activities of these liposome-nucleic acid formulations have been extensively verified in vivo and in vitro.

Despite recent progress, there remains a need in the art to improve the compositions of the liposome-nucleic acid formulation, so as to enable them suitable for general therapeutic applications. Preferably, these compositions would encapsulate nucleic acid with high-efficiency, have high drug: lipid ratios, protect the encapsulated nucleic acid from degradation by intracellular nuclease, suitable for systemic delivery, and facilitate intracellular delivery of the encapsulated nucleic acid. In addition, these liposome-nucleic acid formulations should be well-tolerated and provide appropriate therapeutic index, such as an effective dose of the nucleic acid and no significant toxicity to the patient. The present invention provides such liposome formulations, methods of preparing the liposome formulations, and methods of using the liposome formulations to introduce nucleic acids into mammal cells, for the treatment of human diseases.

SUMMARY OF THE INVENTION

The present invention is to provide a liposome formulation with simplicity for preparation and ease of delivery to the target tissues, which can be used to treat associated diseases caused by abnormal gene expression.

For the purpose of the present invention, the liposome formulation of the present invention comprises complementary cationic lipid pairs, phospholipids, and long-circulating lipids.

Preferably, the liposome formulation comprises 20-80% of the complementary cationic lipid pairs, 10% of the phospholipids, and 10% of the long-circulating lipids, on a molar basis.

Preferably, the complementary cationic lipid pairs include a first cationic lipid and a second cationic lipid, the respective molar percentages of the first cationic lipid and the second cationic lipid are 20~60% in the formulation; the first cationic lipid is heptatriaconta-6,9,28,31-tetraen-19-yl-4-(dimethylamino)-butanoate (CL01) or N,N-dimethyl-(2,3-dilinoleyloxy)propylamine (DLinDMA), the second cationic lipid is cholesteryl 3-(dimethylamino)propanoate (CL06) or cholesteryl 2-(dimethylamino)acetate (CL08).

Preferably, the phospholipid is distearyl phosphatidyl choline (DSPC).

Preferably, the long-circulating lipid is one of N-[(methoxy poly(ethylene glycol)2000)carbamoyl]-1,2-dimyristyloxypropyl-3-amine (PEG-c-DMA), heptatriaconta-6,9,28,31-tetra-en-19-ol methoxy poly(ethylene glycol)2000 carbamate (PEG-DLM), cholesterol methoxy poly (ethylene glycol)2000 carbamate (PEG-Chol), or nonacosan-15-ol methoxy poly (ethylene glycol)2000 carbamate (PEG-DMM).

Preferably, the liposome formulation of the present invention further comprises a therapeutic agent.

Further, the therapeutic agent is a nucleic acid that is one of functional RNAs, their chemically modified structures and mimics, and DNAs, their chemically modified structures and mimics, or their combination.

Further, the functional RNAs are one of siRNAs, miRNAs, small ligand RNAs, and RNA aptamers, or their combination.

The present invention also provides a method of preparing the above liposome formulation, comprising mixing the complementary cationic lipid pairs with the phospholipid and the long-circulating lipid to generate pre-formed vesicles; and then mixing the pre-formed vesicles with the nucleic acid solution to generate the liposome-nucleic acid formulation.

The liposome-nucleic acid formulation may be formed through mixing aqueous solution of siRNAs with cationic lipid dissolved in organic solvents (such as the solvent consisting of the ethanol and a solvent miscible with the ethanol). The nucleic acid mixture comprising cationic lipid can be used directly as pharmaceutical formulation or can be refrigerated until use. Also, the nucleic acid mixture comprising cationic lipid can be chemically processed using the methods commonly used by the skilled in the art. The cationic lipid complex may be appropriately processed using a variety of mechanical methods so as to form solid or liquid nucleic acid drugs.

The present invention also provides use of the liposome formulation as mentioned above in the treatment of diseases caused by abnormal gene expression.

The liposome formulation of the present invention may be used for in vivo delivery of the pharmaceutically acceptable nucleic acid molecules, such as siRNAs or miRNAs. This formulation may be used to prevent and treat diseases in mammals with enhanced efficiency.

DETAILED DESCRIPTION OF THE INVENTION

Figure 1:
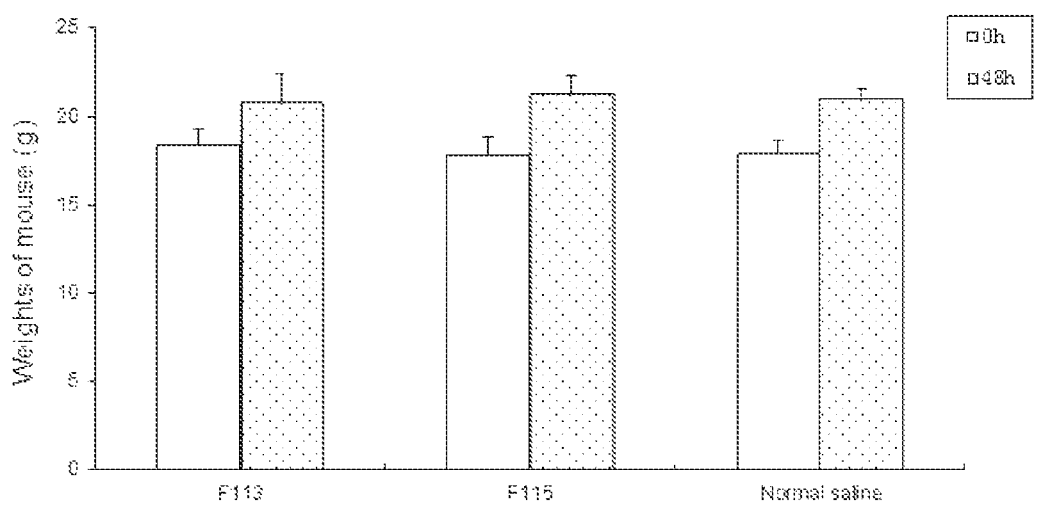
FIG. 1 is a bar graph depicting the body weights of the mice before and after administration of liposome formulations F113 and F115. The horizontal axis represents the experimental groups and the vertical axis represents the body weights of the mice.

In order that the invention may be fully understood, hereby order the preferred embodiment and the following detailed description with accompanying drawings.

EXAMPLE 1

Preparation of heptatriaconta-6,9,28,31-tetra-en-19-ol (DLM, 6a)

Step 1: Synthesis of linoleyl alcohol 2, according to the following reaction formula.

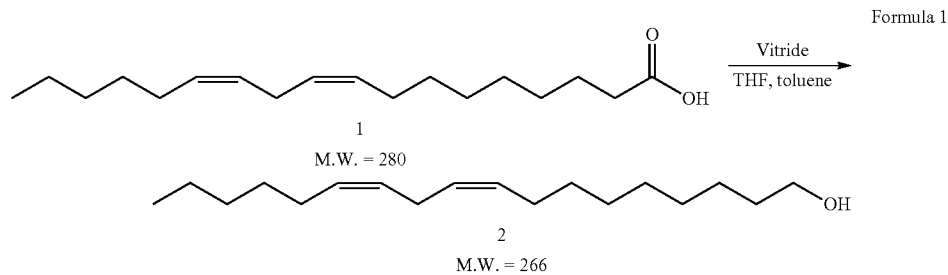

Formula 1

A 1 L glass reactor fitted with an argon inlet was purged with dry argon, and charged with or linoleic acid (30 g, 107 mmol) and THF (320 mL). The reaction mixture was cooled to 0° C. with acetone-dry-ice mixture. While maintaining the reaction temperature below 0° C., 73 mL of sodium bis (2-methoxyethoxy) aluminum hydride solution in methyl-benzene (60% wt/vol) was added drop wise. After the completion of addition, the reaction mixture was incubated at ambient temperature for 2 hours. After reaction, the reaction mixture was cooled to 0° C. To the reaction mixture, a saturated sodium sulfate solution (prepared by dissolving 5.75 g Na$_2$SO$_4$ in 7.85 mL of water) was added drop wise over a period of more than 45 minutes; then, 130 mL of ethyl acetate was added drop wise to the reaction over a period of 30 minutes, with violent stir. The reaction mixture was filtered and the residues were washed with ethyl acetate. The organic layers were combined and concentrated. The resulting product was dissolved in 90 mL of ethyl acetate and washed twice with 45 mL of water, and dried over anhydrous sodium sulfate. Then, the solution was filtered, the organic layer was concentrated to remove the organic solvent with a vacuum pump, resulted in 28.8 g of product 2.

Step 2: Synthesis of linoleyl methanesulfonate 3, the reaction formula is as the following.

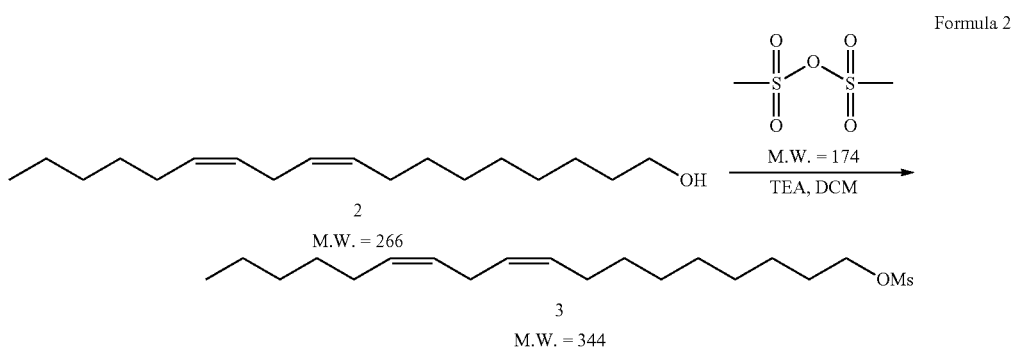

Formula 2

A 500 mL glass reactor fitted with an argon inlet was purged with dry argon, charged with 25 g (94 mmol) of product 2 obtained from the previous step and 210 mL of dichloromethane (DCM), followed by addition of 53 mL of triethylamine (TEA) and 1.15 g (2.0 mol) of DMAP. The reaction mixture was cooled down to −10° C. with acetone-dry ice mixture. While maintaining the reaction temperature below 0° C., a methanesulfonic anhydride solution (prepared by dissolving methanesulfonic anhydride (32.7 g, 188 mmol) in DCM (45 mL)) was added drop wise over a period of more than 1 hour. After the completion of addition, the mixture was incubated at 0° C. for 1 hour. Then, 80 mL of ice-water was added in the reaction mixture, the aqueous layer was extracted by 45 mL of DCM. The organic layers were combined, and the combined organic layer was washed twice with diluted HCl solution (prepared by dissolving 9 mL HCl in 36 mL of water) (2×45 mL), once with water (2×35 mL), and once with brine solution (prepared by dissolving 50 g NaCl in 45 mL of water) (45 mL), then dried over sodium sulfate (12.5 g). Then, the organic layer was concentrated to remove the organic solvent with a vacuum pump, resulted in 32.3 g of product 3.

Step 3: Synthesis of linoleyl bromide 4, the reaction formula is as the following.

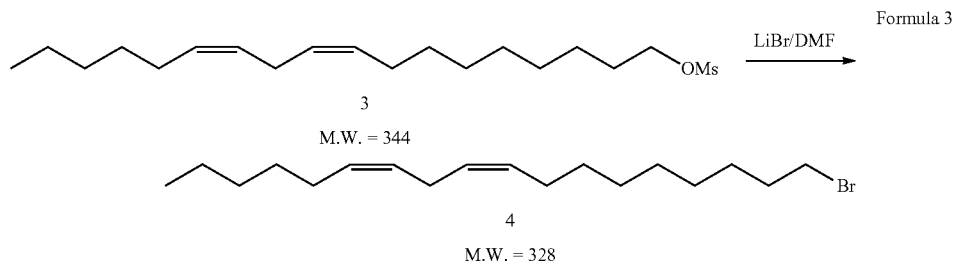

Formula 3

A 500 mL glass reactor fitted with an argon inlet was purged with dry argon, charged with 110 mL of DMF and 30 g (87 mmol) of product 3. This reaction mixture was cooled to −10° C. with acetone-dry-ice mixture. To the stirred reaction mixture, a LiBr solution (prepared by dissolving 11.5 g (132 mmol) LiBr in 110 mL of DMF) was added drop wise, while maintaining the reaction temperature below 0° C. After the completion of addition, the reaction mixture was heated to 45° C. and incubated for 18-20 hours under stirring. After the completion of reaction, 300 mL of water was added into the reaction mixture and the reaction mixture was extracted with 240 mL of n-hexane. The organic layers were combined, washed with 2×45 mL of brine solution (prepared by dissolving 59 g NaCl in 45 mL of water), and dried over $Na_2SO_4$ (17 g). The organic layer was filtered and condensed using a vacuum pump to remove the organic solvent, resulted in a crude product of 27.5 g. The crude product was purified by column chromatograph using 60-120 mesh silica gel (using n-hexanes as mobile phase), and resulted in 23 g of pure product 4 (the yield of the three steps is 81%). $^1$H-NMR (CDCl3, 400 MHz), δ=5.41-5.29 (m, 4H), 4.20 (d, 2H), 3.40 (t, 2H), 2.77 (t, 2H), 2.09-2.02 (m. 4H), 1.88-1.00 (m, 2H), 1.46-1.27 (m, 18H), 0.88 (t, 3H).

Step 4: Synthesis of heptatriaconta-6,9,28,31-tetra-en-19-ol (6a), according to the following reaction formula.

reactor within 1 hour, while maintaining a gentle reflux of the mixture. After the completion of the addition, the reaction mixture was heated to keep reflux for 1 hour. After the raw materials were completely consumed, the reaction mixture was cooled to below 10° C. using an ice-bath, in which a diethyl ether solution of ethyl formate (prepared by dissolving 2.2 mL of ethyl formate in 32 mL of diethyl ether) was added slowly. The reaction mixture was warmed to room temperature and incubated for 1 hour under stirring. Then ice-cold water (56 mL) and 10% sulfuric acid solution (prepared by dissolving 27.2 mL of sulfuric acid in 272 mL of ice-cold water) were added, from which the organic layers were separated. The aqueous layer was extracted with diethyl ether (3×80 mL). The combined organic layers were washed with brine solution (80 ml), dried over sodium sulfate (16 g) and filtered. The organic layer was concentrated and organic solvent was removed with a vacuum pump to obtain a crude product (a mixture of alcohols and formate). This crude product was redissolved in 100 mL of THF. To this a solution of NaOH (prepared by dissolving 7.5 g of NaOH in 150 mL of water) was added and the contents were heated to and incubated at 65° C. for 18 hours. After the completion of the reaction, the reaction mixture was

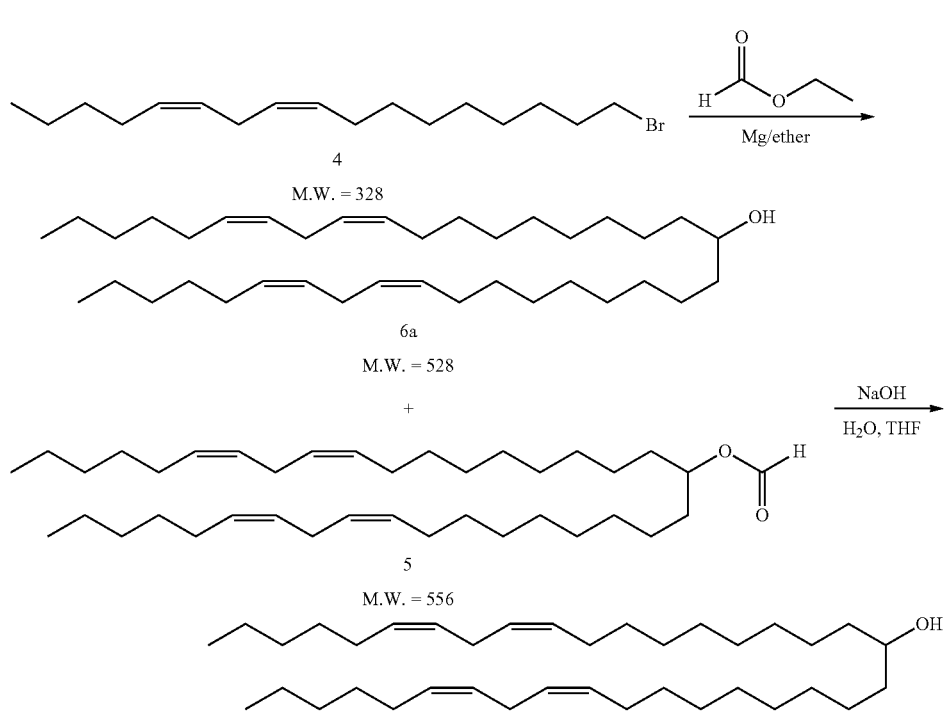

Formula 4

A 250 mL three-neck reactor was purged with dry argon, into which 2.21 g (92 mmol) of activated Mg and 12 mL of anhydrous diethyl ether were added. Product 4 (20 g, 61 mmol) was dissolved in anhydrous diethyl ether (40 mL). Under the protection of argon, 8 mL of the product 4 solution was added to the reactor, together with 0.2 mL (2.8 mmol) of dibromomethane. Using a water bath, the temperature of the reaction mixture was increased to 40° C. After the start of the reaction, the heating resource was removed, and the remaining solution (32 mL) was added drop wise to the cooled to room temperature and extracted with diethyl ether (3×100 mL). The combined organic layers were washed with brine solution (40 mL), dried over sodium sulfate (40 g) and filtered. The organic layer was concentrated. The thus obtained crude product was purified using a 60-120 mesh silica gel (4% ethyl ether in hexane), to obtain the pure product 6a (11.6 g, 80% yield). $^1$H-NMR (CDCl3, 400 MHz), δ=5.47-5.24 (m, 8H), 3.70-3.50 (m, 1H), 2.85-2.66 (m, 4H), 2.12-1.91 (m, 9H), 1.55-1.17 (m, 46H), 0.90-0.80 (m, 6H).

The overall reaction equation is as the following:

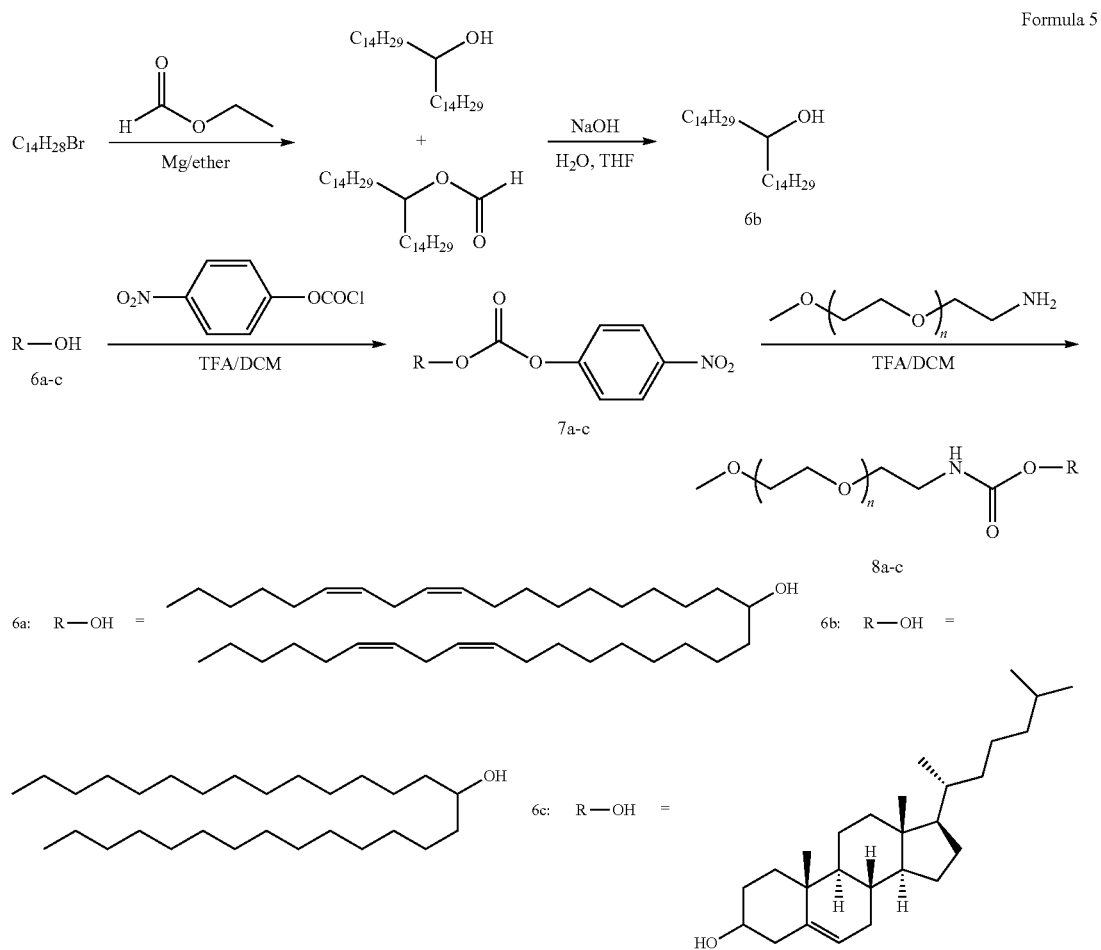

Formula 5

EXAMPLE 2

The synthesis procedure of heptatriaconta-6,9,28,31-tetra-en-19-ol methoxy poly(ethylene glycol)2000 carbamate (PEG-DLM, 8a) comprises the following steps:

Step 1. Synthesis of dilinoleylmethyl p-nitrophenyl carbonate (7a)

0.6 g (1.1 mmol) of dilinoleyl methanol (6a) was added into a 100 ml reactor and dissolved in 20 mL of anhydrous DCM, followed by addition of 4-nitrophenyl chloroformate (0.4 g, 2.0 mmol) and 0.8 mL of TEA. The reaction mixture was incubated at room temperature overnight. After the completion of reaction, the reaction mixture was washed with saturated brine solution (30 mL×3), dried over anhydrous sodium sulfate, and filtered. The solvent was spin-dried to obtain a crude product. The obtained crude product was purified by column chromatograph (using a 4% diethyl ether solution in n-hexane as mobile phase), to obtain product 7a (0.57 g, yield 74.7%).

Step 2: Synthesis of dilinoleyl methanol methoxy poly(ethylene glycol)2000 carbamate (PEG-DLM) (8a)

Into a 100 mL glass reactor, dilinoleylmethyl 4-nitrophenyl carbonate (7a) (7a, 0.45 g, 0.65 mmol) and dioxane (25 mL) were added. After the dissolving of the raw materials, methoxy-polyethylene glycol amine (0.87 g, 0.43 mmol) was added. The reaction mixture was incubated at room temperature for 2 days. Then, the reaction mixture was washed with saturated brine solution (30 mL×3), dried over anhydrous sodium sulfate, and filtered. The solvent was spin-dried, to obtain a crude product. The crude product was purified by column chromatograph (using a 0-4% methanol solution in DCM as mobile phase), to obtain product 8a (0.7 g, yield 59.8%). $^1$H-NMR (CDCl$_3$, 400 MHz), δ=5.46-5.23 (m, 8H), 3.70-3.20 (PEG-CH$_2$), 2.80-2.70 (m, 4H), 2.10-2.00 (m, 8H), 1.50-1.10 (m, 46H), 0.95-0.75 (m, 6H).

EXAMPLE 3

The synthesis procedure of nonacosan-15-ol methoxy poly(ethylene glycol)$_{2000}$ carbamate (PEG-DMM, 8b) comprises the following steps:

Step 1: Synthesis of dimyristyl methanol (6b)

A 250 mL glass reactor with three-neck was purged with dry argon, followed by addition of activated Mg (2.21 g, 92 mmol) and anhydrous diethyl ether (12 mL). A 1-bromo-tetradecane solution was prepared by dissolving 20 g (72 mmol) of 1-bromo-tetradecane in 40 mL of anhydrous diethyl ether. Under the protection of argon, the 1-bromotetradecane solution (8 mL) and dibromomethane (0.2 mL, 2.8 mmol) were added to the reactor. Using a water bath, the temperature of the reactor was increased to 40° C. After the initiation of reaction, the heating resource was removed, the remaining solution (32 mL) was added drop wise to the reactor within 1 hour, while maintaining a gentle reflux of the mixture. After the completion of addition, the reaction mixture was heated to keep reflux for 1 hour. After the raw materials were completely consumed, the reaction mixture was cooled to below 10° C. using an ice-bath, into which a diethyl ether solution of ethyl formate (prepared by dissolving 2.2 mL of ethyl formate in 32 mL of diethyl ether) was added drop wise in more than 1 hour. After the completion of addition, the reaction mixture was incubated at room temperature for 1 hour. Then ice-cold water (56 mL) and 10% sulfuric acid solution (prepared by dissolving 27.2 mL of sulfuric acid in 272 mL of ice-cold water) was added. The organic phase was separated, and the aqueous phase was extracted with diethyl ether (3×80 mL). The organic phases were combined, and the combined organic phases was washed with brine solution (80 ml), dried over sodium sulfate (16 g) and filtered. Then, the organic phase was concentrated and the organic solvent was removed with a vacuum pump, to obtain a crude product (a mixture of alcohols and formate). The crude product was dissolved in 100 mL of THF, in which a NaOH solution (prepared by dissolving 7.5 g of NaOH in 150 mL of water) was added. The reaction mixture was heated to and incubated at 65° C. for 18 hours. After the completion of reaction, the reaction mixture was cooled to room temperature and extracted with diethyl ether (3×100 mL). The organic phases were combined, and the combined organic phase was with brine solution (40 mL), dried over sodium sulfate (40 g), filtered and concentrated, to obtain a crude product. The crude product was purified with a 60-120 mesh silica gel (4% ethyl ether in hexane), to obtain pure product (6b) of 5.5 g. The yield was 35.9%. $^1$H-NMR (CDCl$_3$, 400 MHz), δ=3.70-3.50 (m, 1H), 1.55-1.35 (m, 4H), 1.35-1.20 (m, 48H), 0.90-0.80 (m, 6H).

Step 2: synthesis of dimyristylmethyl 4-nitrophenyl carbonate (7b)

Into a 100 mL glass reactor, 0.6 g (1.4 mmol) of nonacosanol (6b) was added and dissolved in 25 mL of anhydrous DCM, following by addition of 4-nitrophenyl chloroformate (0.93 g, 4.3 mmol) and TEA (0.8 mL). The reaction mixture was incubated at room temperature overnight. After the completion of reaction, the reaction mixture was washed with saturated brine solution (30 mL×3), dried over anhydrous sodium sulfate, and filtered. The solvent reagent was spin-dried, to obtain a crude product. The crude product was purified by column chromatograph (using a 4% diethyl ether solution in n-hexane as mobile phase), to obtain product 7b (0.56 g, yield 66.3%). $^1$H-NMR (CDCl$_3$, 400 MHz), δ=8.35-8.25 (m, 2H), 7.45-7.35 (m, 2H), 4.90-4.80 (m, 1H), 1.8-1.6 (m, 4H), 1.50-1.20 (m, 48H), 0.90-0.75 (m, 6H).

Step 3: synthesis of nonacosan-15-ol methoxy poly(ethylene glycol)2000 carbamate (PEG-DMM) (8b)

Into a 100 mL glass reactor, dimyristylmethyl 4-nitrophenyl carbonate (7b, 0.50 g, 0.83 mmol) and DCM (20 mL) were added. After the raw materials were competently dissolved, methoxy polyethylene glycol amine (0.8 g, 0.40 mmol) was added. The reaction mixture was incubated at room temperature for 2 days. Then, the reaction mixture was washed with saturated brine solution (30 mL×3), dried the reaction mixture over anhydrous sodium sulfate, and filtered. The solvent was spin-dried, to obtain a crude product. The crude product was purified by column chromatograph (using a 0-4% methanol solution in DCM as mobile phase), to obtain product 8b (0.48 g, yield 46.2%). $^1$H-NMR (CDCl$_3$, 400 MHz), δ=4.75-4.65 (m, 1H), 3.70-3.20 (m, PEG-CH$_2$), 1.8-1.6 (m, 4H), 1.50-1.20 (m, 48H), 0.90-0.75 (m, 6H).

EXAMPLE 4

The synthesis procedure of cholesterol methoxy poly (ethylene glycol)$_{2000}$ carbamate (PEG-Chol, 8c) comprises the following steps:

Step 1: Synthesis of cholesteryl 4-nitrophenyl carbonate (7c)

Into a 100 mL glass reactor, cholesterol (6c, 0.6 g, 1.5 mmol) was added and dissolved in anhydrous DCM (20 mL), followed by addition of 4-nitrophenyl chloroformate ester (0.62 g, 3.1 mmol) and TEA (0.8 mL). The reaction system was incubated at room temperature overnight. After the completion of reaction, the reaction mixture was washed with saturated brine (30 mL×3), dried over anhydrous sodium sulfate, and filtered. The solvent was spin-dried, to obtain a crude product. The crude product was purified by column chromatograph (using a 4% diethyl ether solution in n-hexane as mobile phase), to obtain product 7c (0.35 g, yield 42.3%). $^1$H-NMR(CDCl$_3$, 400 MHz), δ=8.35-8.25 (m, 2H), 7.45-7.35 (m, 2H), 5.55-5.45 (m, 1H), 4.65-4.50 (m, 1H), 2.50-0.80 (m, 40H), 0.65-0.60 (m, 3H).

Step 2: Synthesis of cholesterol methoxy poly(ethylene glycol)2000 carbamate (PEG-Chol) (8c)

Into a 100 mL glass reactor, cholesteryl 4-nitrophenyl carbonate 7c (0.30 g, 0.54 mmol) and DCM (20 mL) were added. After the raw materials were dissolved, methoxy polyethylene glycol amine (1.0 g, 0.50 mmol) was added. The reaction mixture was incubated at room temperature for 2 days. The reaction mixture was washed with saturated brine (30 mL×3), dried over anhydrous sodium sulfate and filtered. Then, the solvent was spin-dried, to obtain a crude product. The crude product was purified with a column chromatograph (using a 0-4% methanol solution in DCM as mobile phase), to obtain product 8c (0.60 g, yield 47.0%). $^1$H-NMR (CDCl$_3$, 400 MHz), δ=5.55-5.45 (m, 1H), 4.65-4.50 (m, 1H), 3.40-3.20 (m, PEG-CH$_2$), 2.50-0.80 (m, 40H), 0.65-0.60 (m, 3H).

EXAMPLE 5

Synthesis of heptatriaconta-6,9,28,31-tetraen-19-yl-4-(dimethylamino)-butanoate (CL01), according to the following reaction formula.

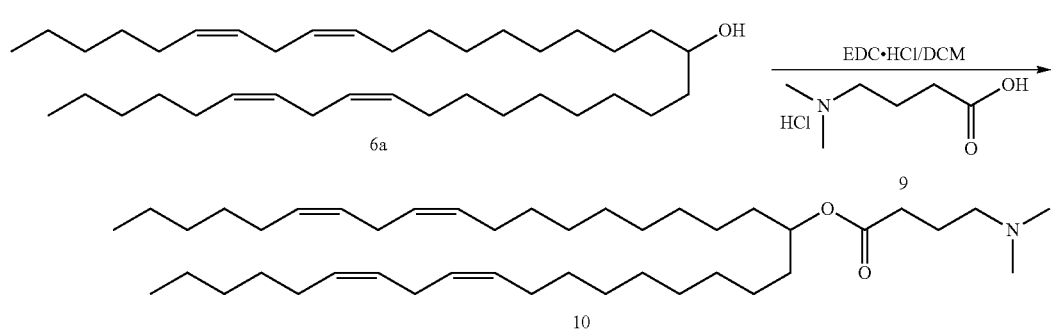

Into a 100 mL glass reactor, product 6a (5 g, 9.5 mmol) was added and dissolved in 40 mL of DCM, following by addition of material 9 (4-(dimethylamino) butyric acid hydrochloride salt) (1.9 g, 11.4 mmol), diisopropylethylamine (2.5 mL), and DMAP (0.14 g, 1.4 mmol). After stirred the reaction mixture for 5 min at room temperature, EDC.HCl (2.78 g, 14.5 mmol) was added, then the reaction mixture was stirred overnight at room temperature. After the completion of reaction, the mixture was diluted with 20 mL of DCM, washed with saturated $NaHCO_3$ (16 mL), water (16 mL) and brine solution (16 mL), dried over anhydrous $Na_2SO_4$, and filtered. The organic phase was concentrated, to obtain a crude product of about 6.25 g. The crude product was purified with a Flash column (packed the column with 90 g of silica gel, and 210 mL of 0.1% TEA in DCM; mobile phases were: 140 mL of 0.1% TEA solution in DCM; 560 mL solution comprising 2% of methanol and 98% of 0.1% TEA solution in DCM; 140 mL solution comprising of 2.5% of methanol and 97.5% of 0.1% TEA solution in DCM; 420 mL solution comprising 3% methanol and 97% of 0.1% TEA solution in DCM), to obtained pure product 10 (CL01, 5.5 g, 91%) as a colorless oil. $^1$H-NMR ($CDCl_3$, 400 MHz), δ=5.47-5.24 (m, 8H), 4.93-4.77 (m, 1H), 2.85-2.66 (m, 4H), 2.37-2.22 (m, 4H), 2.12-1.91 (m, 9H), 1.85-1.69 (m, 2H), 1.49 (d, J=5.4, 4H), 1.39-1.17 (m, 39H), 0.90-0.80 (m, 6H).

EXAMPLE 6

Synthesis of cholesteryl 3-(dimethylamino)propanoate (CL06), according to the following reaction formula.

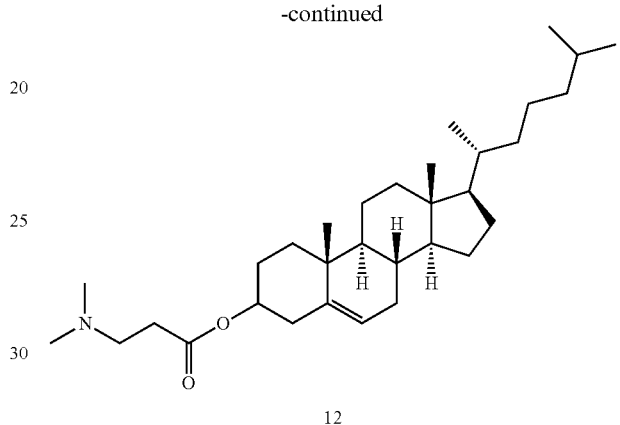

Into a 100 ml glass reactor, cholesterol (1.1 g, 2.84 mmol) dissolved in DCM (20 mL) was added, followed by addition of raw material 11 (3-(dimethylamino) propionic acid hydrochloride, 0.7 g, 4.55 mmol), diisopropylethylamine (1 mL), and DMAP (0.056 g, 0.56 mmol). After stirred the mixture for 5 min at room temperature, EDC.HCl (1.1 g, 5.6 mmol) was added, then the reaction mixture was stirred overnight at room temperature. After the completion of reaction, the reaction mixture was diluted with DCM (20 mL), washed with saturated $NaHCO_3$ (16 mL), water (16 mL), and brine (16 mL), dried over anhydrous $Na_2SO_4$ and filtered. The organic phase was concentrated, to obtain a crude product of about 1.1 g. The crude product was purified with a Flash column (packed the column with 90 g of silica gel and 210 mL of 0.1% TEA in DCM; mobile phases were: 140 mL of 0.1% TEA solution in DCM; 560 mL solution comprising 2% of methanol and 98% of 0.1% TEA solution in DCM; 140 mL solution comprising of 2.5% of methanol and 97.5% of 0.1% TEA solution in DCM; 420 mL solution comprising 3% methanol and 97% of 0.1% TEA solution in DCM), to obtained pure product 12 (CL06, 600 mg, 43.6%). $^1$H-NMR ($CDCl_3$, 400 MHz), δ=5.55-5.45 (m, 1H), 4.65-4.50 (m, 1H), 2.6 (m, 2H), 2.5 (m, 2H), 2.3 (m, 2H), 2.2 (m, 6H), 2.50-0.80 (m, 28H), 0.65-0.60 (m, 3H).

EXAMPLE 7

Synthesis of cholesteryl 2-(dimethylamino)acetate (CL08), according to the following reaction formula.

Formula 8

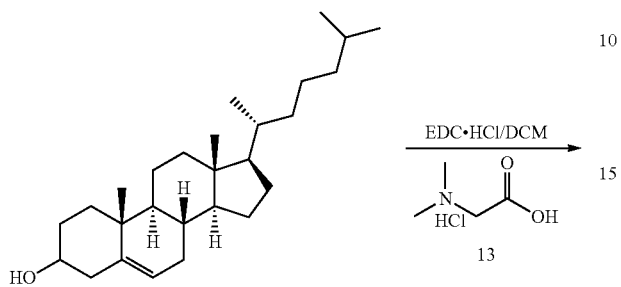

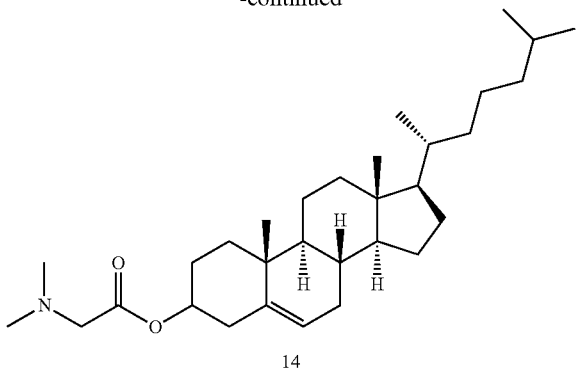

Into a 100 mL glass reactor, the reaction product cholesterol (1.1 g, 2.84 mmol) dissolved in DCM (20 mL) and raw material 13 (2-(dimethylamino) acetic acid hydrochloride, 0.7 g, 5.0 mmol) were added, following by addition of diisopropylethylamine (1 mL) and DMAP (0.056 g, 0.56 mmol). After stirred the reaction mixture for 5 min at room temperature, EDC.HCl (1.1 g, 5.6 mmol) was added, and then the reaction mixture was stirred overnight at room temperature. After the completion of reaction, the reaction mixture was diluted with DCM (20 mL), washed with of saturated $NaHCO_3$ (16 mL), water (16 mL) and brine (16 mL), dried over anhydrous $Na_2SO_4$, and filtered. The organic phase was concentrated, to obtain a crude product of about 1.1 g. The crude product was purified with a Flash column (packed the column with 90 g of silica gel and 210 mL of 0.1% TEA in DCM; mobile phases were: 140 mL of 0.1% TEA solution in DCM; 560 mL solution comprising 2% of methanol and 98% of 0.1% TEA solution in DCM; 140 mL solution comprising of 2.5% of methanol and 97.5% of 0.1% TEA solution in DCM; 420 mL solution comprising 3% methanol and 97% of 0.1% TEA solution in DCM), to obtained pure product 14 (CL08, 1000 mg, 74.6%). $^1$H-NMR (CDCl$_3$, 400 MHz), δ=5.55-5.45 (m, 1H), 4.65-4.50 (m, 1H), 3.3 (m, 2H), 2.4 (m, 6H), 2.50-0.80 (m, 28H), 0.65-0.60 (m, 3H).

EXAMPLE 8

Synthesis of 1,2-Dilinoleyloxy-N,N-dimethyl-3-aminopropane (DLinDMA), according to the following reaction formula.

Formula 9

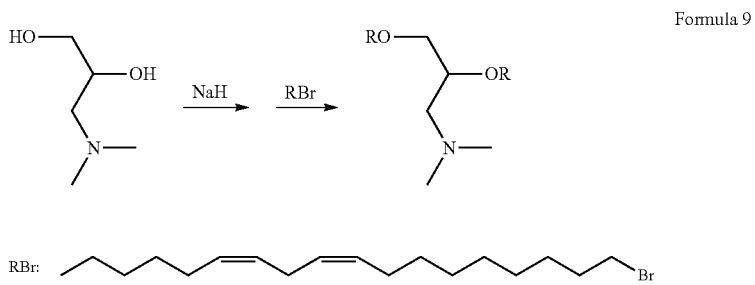

Under the protection of nitrogen, NaH (986 mg, 80%, 32.3 mmol) and anhydrous benzene were added into a 100 mL glass reactor. Keeping stirring the reaction reactor, 3-(N, N-dimethylamino)-propanediol (401 mg, 33.7 mmol) dissolved in anhydrous benzene (10 mL) was added, then continuously stirred the reaction mixture for 15 min at room temperature. A linoleyl bromide solution was prepared by dissolving linoleyl bromide (3 g, 9.15 mmol) in anhydrous benzene (16 mL), the resulted solution was added in the reaction in drop wise. The reaction was incubated and stirred for 30 mins at room temperature, then heated to reflux for 2 days. After the completion of reaction, the reaction mixture was cooled to room temperature, and treated with 40 mL of a mixture of toluene and ethanol (1:1). The organic phase was washed twice with water (25 mL) and saturated brine solution (30 mL), dried over anhydrous sodium sulfate. The solvent was evaporated, to obtain a crude product of 3.1 g. The crude product was purified with a Flash column (using MeOH/DCM (0-3%) as mobile phase), to obtain pure product (1.1 g, 39.1%). $^1$H-NMR (CDCl$_3$, 400 MHz), δ=5.47-5.24 (m, 8H), 3.65-3.5 (m, 7H), 2.85-2.66 (m, 4H), 2.45 (m, 2H), 2.3 (s, 6H), 2.1 (m, 8H), 1.5 (m, 4H), 1.4-1.2 (m, 38H), 0.9 (t, 6H).

EXAMPLE 9

The synthesis procedure of N-[(methoxy poly(ethylene glycol)2000)carbamoyl]-1,2-dimyristyloxypropyl-3-amine (PEG-c-DMA) comprises the following steps:

Step 1: Synthesis of DMA, according to the following reaction formula.

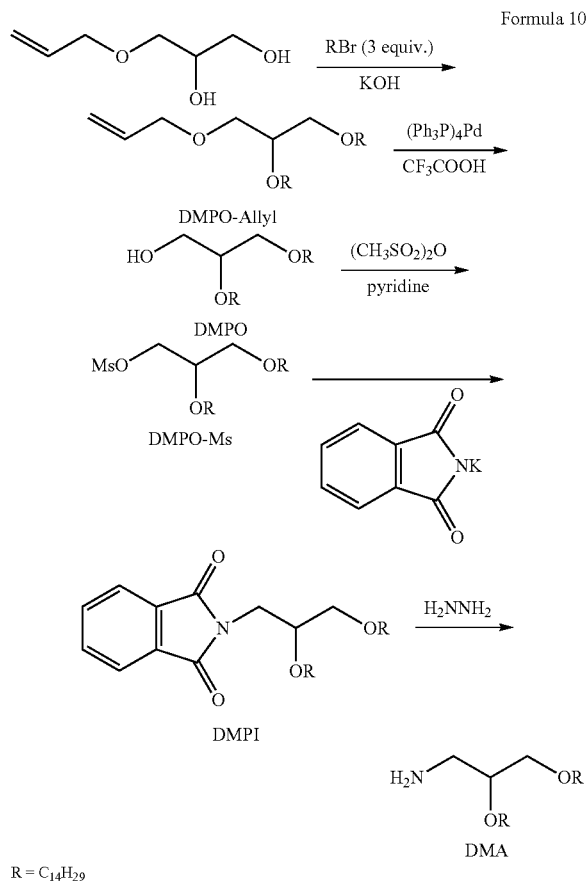

R = C$_{14}$H$_{29}$

1. The Preparation of DMPO-Allyl

The mixture of 3-allyloxy-1,2-propanediol (9.24 g, 70 mmol), 1-bromo-tetradecane (61.0 g, 213 mmol), and potassium hydroxide (16 g, purity 90%) was added in 500 mL of anhydrous benzene. Under the protection of argon (Ar), the reaction mixture was refluxed overnight (17 hrs), using a Dean-Stark apparatus to remove water. After the reaction mixture was cooled to room temperature, it was diluted with benzene (200 mL). The organic phase (oil phase) was extracted three times with water (3×150 mL) and twice with strong brine solution for (2×150 mL), dried over anhydrous magnesium sulfate. The solvent was removed under vacuum condition, to obtain a clear yellow oil of 56 g. The product was purified with a silica gel column (particle size 230-400 mesh, 1400 mL), using 0-5% ethyl acetate/hexane gradient as a mobile phase. The final product was 35 g of DMPO-Allyl, with yield of 95%.

2. The Preparation of DMPO

Trifluoroacetic acid (40 mL) was added in a DMPO-Allyl solution prepared by dissolving DMPO-Allyl (30 g, 57 mmol) in ethanol (500 mL), followed by addition of tetrakis (triphenylphosphine) palladium (9.0 g, 7.8 mmol). The reactor was purged with argon (Ar) and maintained reflux overnight (16 hrs), kept away from light. After refluxing, the solvent was removed under vacuum condition, to obtain an oil of brown. The crude product was purified with a silica gel column (particle size of 230-400 mesh, 1400 mL, using 0-1% methanol/DCM gradient as mobile phase). The final product was DMPO of 17.8 g, a yellowish wax. The yield was 64%.

3. The Preparation of DMPO-Ms

Under the protection of argon (Ar), pyridine (6 mL, 74 mmol) was added drop wise to a methanesulfonic anhydride solution prepared by dissolving methanesulfonic anhydride (13.0 g, 96% purity, 71.6 mmol) in anhydrous dichloromethane (150 mL). To this suspension, a DMPO solution prepared by dissolving DMPO (17.8 g, 36.7 mmol) in anhydrous dichloromethane (150 mL) was added. Under the protection of argon (Ar), the reaction mixture was stirred overnight (17 hrs), at room temperature. After the completion of reaction, the reaction mixture was diluted with dichloromethane (200 mL), extracted three times with water (200 mL) and one time with strong brine solution (200 mL), dried over anhydrous magnesium sulfate (MgSO$_4$). The solvent was removed by evaporation, to obtain a crude product DMPO-Ms of 20.9 g, as a yellow waxy. Without further purification, the crude product was used as a reactant in the next step.

4. The Preparation of DMPI

The crude product DMPO-Ms (20.8 g, 37 mmol) obtained from the previous step was dissolved in 400 ml of DMF, mixed with potassium phthalimide (18 g, 97 mmol), stirred at 70° C. overnight (20 hrs) under argon (Ar) atmosphere, to obtain a yellow suspension. The suspension was cooled to room temperature and poured into 800 mL of ice-cold water. The aqueous phase was extracted three times with ethyl acetate (350 mL), and the organic phases was combined, extracted one time with deionized water (300 mL), one time with strong brine solution (300 mL), then dried over anhydrous magnesium sulfate (MgSO$_4$). Under vacuum condition, the solvent was removed to yield a mixture of oil and solid substances. The mixture was dissolved in 500 mL of hexane, from which the insoluble materials was removed by filtering, and rinsed with hexane (100 mL). The filtrate was distilled to obtain a waxy crude product of 19.6 g. The crude product was purified with a silica gel column (particle size of 230-400 mesh, 600 mL, using a 0-5% ethyl acetate/hexane gradient solution as mobile phase), to obtain a white wax pure product, DMPI of 12.7 g. The yield was 56%.

5. The Preparation of DMA

The said DMPI (12.7 g, 20.7 mmol) and hydrazine hydrate (15.0 mL, 310 mmol) was dissolved in 300 mL of ethanol, refluxed overnight (16 hrs), yielded a large amount of white solid substance. The suspension was cooled to room temperature, filtered and the obtained solid was washed twice with ethanol (100 mL). The filtrate was collected and distilled to remove the ethanol. The residue was dissolved in 500 mL of chloroform, the insoluble substances (white solid) was filtered again and washed once with chloroform (100 mL). The chloroform phases was combined, washed twice with deionized water (200 mL) and once with strong brine solution (200 mL), dried over anhydrous magnesium sulfate. After the solvent was removed by distilling, a light oil-like crude product of 10.1 g was obtained. The crude product was purified with a silica gel column (particle size of 230-400 mesh, 300 mL, using a 0-10% methanol/chloroform gradient solution as mobile phase), to obtain a light oil-like pure product (DMA) of 9.55 g, the yield was 95% yield.

19

Step 2: Synthesis of PEG-c-DMA, according to the following reaction formula.

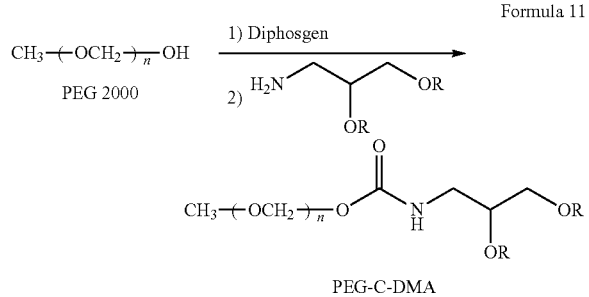

Methoxy-PEG 2000 (28 g, 14 mmol) was dissolved in 150 mL of anhydrous benzene, which was previously distilled to remove residual moisture. The product was dissolved in anhydrous dichloromethane (250 mL). Under argon atmosphere, trichloromethyl chloroformate (6.92 g, 35 mmol) was added, the reaction mixture was stirred for 3 hours at room temperature. After the solvent was distilled off under vacuum condition, anhydrous benzene (150 mL) was added into the reaction mixture, the reaction mixture was distilled to remove the solvent until dryness, under vacuum condition. Under argon atmosphere, a DMA solution was prepared by dissolving DMA (9.5 g, 20 mmol) in anhydrous dichloromethane (200 mL), the DMA solution (200 mL) and then dry triethylamine (3.9 mL, 28 mmol) were added in the reaction mixture. With continuous stirring, the reaction mixture was incubated overnight (18 hours) at room temperature. The reaction product was diluted with dichloromethane (250 mL), and the organic phase was extracted with of 1% HCl solution (200 mL), washed with deionized water (200 mL), 0.1% sodium carbonate solution (200 mL), deionized water (200 mL) and strong brine solution (200 mL), then dried over anhydrous magnesium sulfate. After the solvent was removed by distilling, a crude product (44 g) with a light slurry was obtained. The crude product was purified with a silica gel column (particle size of 230-400 mesh, amount of the silica gel 1600 mL, using a 0-10% methanol/chloroform gradient solution as mobile phase), to obtain a mixture of product PEG-c-DMA and un-reacted DMA, white or yellow wax-like materials. Diethyl ether (150 mL) was added in the wax-like mixture to dissolve the un-reacted DMA. The white solid residue was collected by filtration, washed in drop wise twice with diethyl ether (150 mL), dried under vacuum condition, to obtain a pure product of 30.7 g, in white powder. The yield was 87%. $^1$H NMR (400 MHz, CDCl$_3$) δ:5.11 (1H, m, NH), 4.17 (2H, m, CH$_2$), 3.80-3.1 (8H, m), 3.60 (130H, s, OCH$_2$CH$_2$O), 3.34 (3H, s, OCH$_3$), 2.42 (2H, m, NCH$_2$), 1.49 (4H, m, 2×CH$_2$), 1.21 (44H, s, 22×CH$_2$), 0.84 (6H, t, 2×C$_{H3}$) ppm.

EXAMPLE 10

Preparation of Liposome Formulation F113

1. Reagents, Materials, and Instruments 1.1 Reagents.
1.1.1 Lipids: the first cationic lipid, CL01, prepared in Example 5; the second cationic lipid, CL08, prepared in Example 7; phospholipids, DSPC, purchased from Shanghai

20

Advanced Vehicle Technology Corporation; long-circulating lipid, PEG-c-DMA, prepared in Example 9.
1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.
1.2 ApoB-siRNA, synthesized by Biomics Biotechnologies Co. Ltd and provided as a freeze-dried powder. Sequences of the siRNA are:

ApB-S:   5'-GUCAUCACACUGAAUACCAAU-3' (SEQ ID NO: 1);

ApB-AS:  5'-AUUGGUAUUCAGUGUGAUGACAC-3'
         (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).
1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome formulation 2.1 Reagent preparation
2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.
2.1.2 Formulation buffer (50 mM citric acid, pH4.0): prepared as described in 2.1.1.
2.1.3 Dialysis buffer: 1×phosphate buffer (phosphate-buffered saline, PBS) (Biomics Biotechnologies Co. Ltd).
2.2 Preparation of siRNA stock solution.
2.2.1 siRNA dissolvation: ApoB-siRNA stock solution of 50 mg/mL was prepared with solution of 10 mM citrate/30 mM NaCl, pH6.0.
2.2.2 An aliquot of ApoB-siRNA stock solution was diluted in 2000-fold with PBS, for measuring the concentration of the siRNA. Three parallel measurements were performed for each sample.
2.2.3 Using a UV spectrophotometer, $A_{260}$ value was measured and the actual concentration of ApoB-siRNA in the stock solution was determined. As shown in Table 1, $A_{260}\times 50$ g/mL per OD×2000/1000=64.62 mg/mL.

TABLE 1

$A_{260}$ values of ApoB-siRNA solutions

| Sample | $A_{260}$ value | | Average |
|---|---|---|---|
| 1 | 0.6583 | 0.6631 | 0.6607 |
| 2 | 0.6644 | 0.7015 | 0.6830 |
| 3 | 0.6781 | 0.6786 | 0.6784 |

TABLE 1-continued

A$_{260}$ values of ApoB-siRNA solutions

| Sample | A$_{260}$ value | | Average |
|---|---|---|---|
| 4 | 0.5959 | 0.5985 | 0.5972 |
| 5 | 0.6213 | 0.6241 | 0.6227 |
| 6 | 0.6321 | 0.6389 | 0.6355 |
| | Average | | 0.6462 |

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 2. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 2

The component amounts for F113 formulation
Total volume: 4.0 mL
Volume of ethanol: 1.2 mL; Concentration of ethanol: 30% (v/v)

| Lipid | Concentration (mg/mL) | Amount (mL) |
|---|---|---|
| CL-01 | 40 | 0.300 |
| DSPC | 20 | 0.184 |
| CL08 | 20 | 0.442 |
| PEG-c-DMA | 50 | 0.239 |
| Ethanol further added | | 0.035 |

2.4.2 Preparation of siRNA liposome formulation.

PFV of desired volume was dispensed in a 50 mL Falcon tubes, pre-equilibrated in a 35° C. water bath for 4-5 min. 34 µL ApoB-siRNA stock solution (64.62 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 µL incubation product was used for A$_{260}$ measurement. The resulted liposome formulation was dialyzed overnight in 1×PBS, using a MD24 dialysis bag. The dialyzed product was then recovered, filtered sterilization using a 0.2 syringe filter. 600 µL of the product was measured for its encapsulation efficiency.

2.4.3 Measurement of encapsulation efficiency.

To measure the encapsulation efficiency, free drugs need to be separated from the liposome. A commercial anion exchange micro-column (Vivapure D Mini H) was used in the separation process, during which the negatively-charged free siRNAs were bound by the exchange column due to electrostatic adsorption; while the encapsulated siRNA located within the inside of the cationic liposome, therefore could not be bound by the column. So that, the cationic lipid-encapsulated siRNAs could be separated from the free siRNAs by a simple centrifugation. 300 µL steriled product flew through a Vivapure D Mini H (ion exchange column), according to the manufacturer's instructions so as to perform a separation procedure. The resulted product was the sample after chromatography. The remaining original sample of 300 µL was the sample before chromatography.

1) According to Table 3, the samples for OD measurement (A$_{260}$) were prepared.

TABLE 3

Sample preparation for OD measurement

| Sample | PBS (µL) | Sample (µL) | Chloroform/Methanol (volume ratio 1:2.1) (µL) | Methanol (µL) |
|---|---|---|---|---|
| Blank | 250 | 0 | 750 | 100 |
| Incubation product | 220 | 30 | 750 | 100 |
| Sample before chromatography | 210 | 40 | 750 | 100 |
| Sample after chromatography | 210 | 40 | 750 | 100 |

2) The absorbance at 260 nm wavelength was determined, using an ultraviolet spectrophotometer (n=3, two parallel measurements were performed for each sample). The results are shown in Table 4.

TABLE 4

A$_{260}$ value of liposome formulation F113

| Sample | A$_{260}$ Value | | A$_{260}$ Average | siRNA Con. (mg/mL) |
|---|---|---|---|---|
| Incubation product | 0.2135 | 0.2149 | 0.2316 | 0.4576 |
| | 0.2323 | 0.2318 | | |
| | 0.2483 | 0.2485 | | |
| Sample before chromatography | 0.1816 | 0.1775 | 0.1869 | 0.2770 |
| | 0.1957 | 0.1985 | | |
| | 0.1828 | 0.1851 | | |
| Sample after chromatography | 0.1222 | 0.1228 | 0.1268 | 0.1880 |
| | 0.1246 | 0.1247 | | |
| | 0.1330 | 0.1337 | | |

3) Calculation of the encapsulation efficiency.

Based on the measured A$_{260}$ values, the actual concentration coefficient was calculated. The actual concentration coefficient (mg/mL)=added volume of ApoB-siRNA stock solution (mL)×actual concentration of ApoB-siRNA in the stock solution (mg/mL)×0.03 (mL)×1000/(total volume of siRNA liposome formulation (mL))×A$_{260}$ values of incubation product×1.1 (mL)). The actual concentration coefficient was to be 53.90. Based on this coefficient, the actual siRNA concentration of the incubation product, the samples before chromatography, and the samples after chromatography were calculated and presented in Table 4. Based on the concentration of the siRNA, the encapsulation efficiency is defined as: encapsulation efficiency=(lipid encapsulated-drug/total drug in the preparation of liposome formulation)×100%. The calculation formula is: encapsulation rate=siRNA concentration of sample after chromatography/siRNA concentration of sample before chromatography=0.188/0.277×100%=67.9%. The encapsulation efficiency was 67.9%, ApoB-siRNA concentration in liposome formulation was 0.188 mg/mL.

2.4.4 pKa measurement of the PFVs.

The pKa of the PFV was determined, using a fluorescent dye 6-(4-toluidino)-2-naphthalnesulfonic acid (TNS). In an aqueous solution, this fluorescent dye does not emit light or emit only a weak fluorescence; while in an organic environment, it emits strong characteristic fluorescence, so as to enable the measurement of the pKa of the PFV. When added in a cationic liposome solution, the negatively-charged TNSs will enrich on the surface of the liposome and emit strong characteristic fluorescence; while the unbound TNS does not emit light in the aqueous phase. Therefore, the fluorescence intensity of the solution (within a certain range) is in proportional to the amount of surface positive charge of the liposome. So that, by measuring the fluorescence intensity of the solution, the ionization degree of the amino groups of the cationic liposomes can be determined. According to the definition of the dissociation constant, it is known that when the ionization degree of a weak acid is 50% in a solution, the pH value of the solution is equal to the pKa value of the acid. Therefore if we plot the fluorescence intensity against the pH value of the solution, the pH value of the midpoint of the fluorescence intensity is equal to the apparent pKa of the cationic liposome solution.

The detailed procedures are as follows: 1) In each sample tube, 2 mL PBS solution of different pH values (pH values were 2.5, 3.0, 3.5, 4.0, 4.5, 5.0, 5.5, 6.0, 6.5, 7.0, 7.5, 8.0, 8.5, 9.0, 9.5, 10.0, 10.5 and 11.0, pH values were adjusted with HCl and NaOH) was added. 2) In each sample tube, 80 μL of morpholine ethanol sulfonic solution (250 mM), 80 μL of HEPES solution (250 mM), 80 μL of ammonium acetate solution (250 mM), 80 μL of sodium chloride solution (3.85M), and 60 μL of PFV were sequentially added. 3) In the tube containing sample of pH2.5, 40 mL of TNS solution (83.5 μM) was added. After stirring for 30 s, the solution was taken out and the emission fluorescence intensity was determined using a fluorescence spectrophotometer (excitation wavelength, 321 nm; emission wavelength, 445 nm). 4) Similarly, the emission intensity of TNS was determined at different pH values. Using pH value as x-axis, emission fluorescence intensity as y-axis, the emission fluorescence intensity was plotted against the pH value of the solution. The pH value of the midpoint of the fluorescence intensity is equal to the apparent pKa of the cationic liposome solution. The calculated pKa value of the liposome formulation is 6.55.

2.4.5 Particle size measurement.

With a Nicomp 370 particle sizing system, the sizes of the pre-formed empty vesicles and the siRNA liposome formulation were determined to be 67.92 nm and 63.17 nm, respectively.

EXAMPLE 11

Preparation of Liposome Formulation F115

1. Reagents, Materials, and Instruments 1.1 Reagents.

1.1.1 Lipids: the first cationic lipid, CL01, prepared in Example 5; the second cationic lipid, CL06, prepared in Example 6; phospholipids, DSPC, purchased from Shanghai Advanced Vehicle Technology Corporation; long-circulating lipid, PEG-c-DMA, prepared in Example 9.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:   5'-GUCAUCACACUGAAUACCAAU-3' (SEQ ID NO: 1);

ApB-AS:  5'-AUUGGUAUUCAGUGUGAUGACAC-3'
         (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation): high-speed refrigerated centrifuge (Xiangyi Corporation), fluorescence spectrophotometer (RF-5301PC, Shimadzu Corporation).

2. Preparation of Liposome Formulation 2.1 Reagent preparation 2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, for measuring the concentration of the siRNA. Three parallel measurements were performed for each sample.

2.2.3 Using a UV spectrophotometer, $A_{260}$ value was measured and the actual concentration of ApoB-siRNA in the stock solution was determined as: $A_{260}$×50 g/mL per OD×2000/1000=64.62 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 5. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 5

The component amounts for F115 formulation
Total volume: 4.0 mL
Volume of ethanol: 1.2 mL, concentration of ethanol: 30% (v/v)

| Lipid | Concentration (mg/mL) | Amount (mL) |
|---|---|---|
| CL-01 | 40 | 0.300 |
| DSPC | 20 | 0.185 |
| CL06 | 20 | 0.455 |
| PEG-c-DMA | 50 | 0.239 |
| Ethanol further added | | 0.022 mL |

2.4.2 Preparation of siRNA liposome formulation.

PFV of desired volume was dispensed in a 50 mL Falcon tubes, pre-equilibrated in a 35° C. water bath for 4-5 min. 34 µL ApoB-siRNA stock solution (64.62 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 µL incubation product was used for $A_{260}$ measurement. The resulted liposome formulation was dialyzed overnight in 1×PBS, using a MD24 dialysis bag. The dialyzed product was then recovered, filtered sterilization using a 0.2 µm syringe filter. 600 µL of the product was measured for its encapsulation efficiency.

2.4.3 Measurement of encapsulation efficiency.

300 µL steriled product flew through Vivapure D Mini H (ion exchange column) according to the manufacturer's instructions, so as to perform a separation procedure. The resulted product was the sample after chromatography. The remaining original sample of 300 µL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 6.

TABLE 6

A260 value of liposome formulation F115

| Sample | $A_{260}$ value | $A_{260}$ average | siRNA Con. (mg/mL) |
|---|---|---|---|
| Incubation product | 0.2250 0.2397 0.2482 | 0.2302 0.2399 0.2499 | 0.2388 | 0.4576 |

TABLE 6-continued

A260 value of liposome formulation F115

| Sample | $A_{260}$ value | $A_{260}$ average | siRNA Con. (mg/mL) |
|---|---|---|---|
| Sample before chromatography | 0.1844 0.1849 0.1876 | 0.1871 0.1866 0.1876 | 0.1864 | 0.2678 |
| Sample after chromatography | 0.0972 0.1046 0.1078 | 0.0976 0.1042 0.1077 | 0.1032 | 0.1483 |

3) Calculation of the encapsulation efficiency.

As described in Example 10, the actual concentration coefficient was calculated to be 52.26. Based on this coefficient, the actual siRNA concentration of the incubation product, the samples before chromatography, and the samples after chromatography were calculated and presented in Table 6. Based on the concentrations of the siRNA, the encapsulation efficiency was calculated to be 55.4%, and the concentration of ApoB-siRNA was calculated to be 0.148 mg/mL in liposome formulation.

2.4.4 pKa measurement of the PFVs.

As described in Example 10, pKa of the PFVs was measured to be 7.32.

2.4.5 Particle size measurement.

With a Nicomp 370 particle sizing system, the sizes of the pre-formed empty vesicles and the liposome formulation were determined to be 65.43 nm and 69.37 nm, respectively.

EXAMPLE 12

Preparation of Liposome Formulation F120

1. Reagents, Materials, and Instruments 1.1 Reagents.

1.1.1 Lipids: the first cationic lipid, CL01, prepared in Example 5; the second cationic lipid, CL06, prepared in Example 6; phospholipids, DSPC, purchased from Shanghai Advanced Vehicle Technology Corporation; long-circulating lipid, PEG-DLM, prepared in Example 2.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:  5'-GUCAUCACACUGAAUACCAAU-3' (SEQ ID NO: 1);

ApB-AS: 5'-AUUGGUAUUCAGUGUGAUGACAC-3'
        (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NL1 liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation 2.1.1 siRNA dissolving buffer (10 mM citric acid, 30 mM NaCl, pH6.0): prepared with RNase-free water or water for injection, upon adjusting pH, filtered with 0.22 µm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, for measuring the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260} \times 50$ g/mL per OD×2000/1000=38.51 mg/mL.

TABLE 7

A 260 value of ApoB-siRNA solution

| Sample | $A_{260}$ value | | Average |
|---|---|---|---|
| 1 | 0.3811 | 0.3844 | 0.3828 |
| 2 | 0.3863 | 0.3882 | 0.3873 |
| 3 | 0.3954 | 0.3948 | 0.3951 |
| 4 | 0.3781 | 0.3806 | 0.3794 |
| 5 | 0.3873 | 0.3873 | 0.3873 |
| 6 | 0.3792 | 0.3783 | 0.3788 |
| Average | | | 0.3851 |

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 8. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 8

The component amounts for F120 formulation
Total volume: 4.0 mL
Volume of ethanol: 1.2 mL, concentration of ethanol: 30% (v/v)

| Lipid | Concentration (mg/mL) | Amount (mL) |
|---|---|---|
| CL-01 | 40 | 0.275 |
| DSPC | 20 | 0.169 |
| CL06 | 20 | 0.417 |
| PEG-DLM | 50 | 0.221 |
| Ethanol further added | | 0.117 |

2.4.2 Preparation of siRNA liposome formulation.

PFV of desired volume was dispensed in a 50 mL Falcon tubes, pre-equilibrated in a 35° C. water bath for 4-5 min. 52 µL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 µL incubation product was used for $A_{260}$ measurement. The resulted liposome formulation was dialyzed overnight in 1×PBS, using a MD24 dialysis bag. The dialyzed product was then recovered, filtered sterilization using a 0.2 µm syringe filter. 600 µL of the product was measured its encapsulation efficiency.

2.4.3 Measurement of encapsulation efficiency.

300 µL steriled product flew through Vivapure D Mini H (ion exchange column) according to the manufacturer's instructions, so as to perform a separation procedure. The resulted product was the sample after chromatography. The remaining original sample of 300 µL was the sample before chromatography.

1) According to Table 3, the samples for OD measurement ($A_{260}$) were prepared.

2) The absorbance at 260 nm wavelength, was determined using an ultraviolet spectrophotometer (n=3, two parallel measurements were performed for each sample). The results are shown in Table 9.

TABLE 9

A 260 value of liposome formulation F120

| Sample | $A_{260}$ value | | $A_{260}$ average | siRNA Con. (mg/mL) |
|---|---|---|---|---|
| Incubation product | 0.3256 | 0.3314 | 0.3230 | 0.4170 |
| | 0.3224 | 0.3273 | | |
| | 0.3096 | 0.3196 | | |
| Sample before chromatography | 0.2464 | 0.2482 | 0.2350 | 0.2270 |
| | 0.2252 | 0.2272 | | |
| | 0.2292 | 0.2311 | | |
| Sample after chromatography | 0.0791 | 0.0791 | 0.0760 | 0.0730 |
| | 0.0712 | 0.0729 | | |
| | 0.0750 | 0.0775 | | |

3) Calculation of the encapsulation efficiency.

As described in Example 10, the actual concentration coefficient was calculated to be 35.25. Based on this coefficient, the actual siRNA concentration of the incubation product, the samples before chromatography, and the samples after chromatography were calculated and presented in Table 9. Based on the concentrations of the siRNA, the encapsulation efficiency was calculated to be 55.4%, and the concentration of ApoB-siRNA was calculated to be 0.073 mg/mL in liposome formulation.

2.4.4 pKa measurement of the PFVs.

As described in Example 10, pKa of the PFVs was measured to be 7.42.

2.4.5 Particle size measurement.

With a Nicomp 370 particle sizing system, the sizes of the pre-formed empty vesicles and the siRNA liposome formulation were determined to be 61.85 nm and 111.5 nm, respectively.

EXAMPLE 13

Preparation of Liposome Formulation F121

1. Reagents, Materials, and Instruments 1.1 Reagents.

1.1.1 Lipids: the first cationic lipid, CL01, prepared in Example 5; the second cationic lipid, CL06, prepared in Example 6; phospholipids, DSPC, purchased from Shanghai Advanced Vehicle Technology Corporation; long-circulating lipid, PEG-DMM, prepared in Example 3.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

```
ApB-S:   5'-GUCAUCACACUGAAUACCAAU-3' (SEQ ID NO: 1);

ApB-AS:  5'-AUUGGUAUUCAGUGUGAUGACAC-3'
         (SEQ ID NO: 2).
```

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation 2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS for measuring the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260} \times 50$ g/mL per OD×2000/1000=38.51 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 10. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 10

The component amounts for F121 formulation
Total volume: 4.0 mL
Volume of ethanol: 1.2 mL, concentration of ethanol: 30% (v/v)

| Lipid | Concentration (mg/mL) | Amount (mL) |
|---|---|---|
| CL-01 | 40 | 0.275 |
| DSPC | 20 | 0.169 |
| CL06 | 20 | 0.417 |
| PEG-DMM | 50 | 0.213 |
| Ethanol further added | | 0.125 mL |

2.4.2 Preparation of siRNA liposome formulation.

PFV of desired volume was dispensed in a 50 mL Falcon tubes, pre-equilibrated in a 35° C. water bath for 4-5 min. 52 μL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 6004 incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured for its encapsulation efficiency.

2.4.3 Measurement of encapsulation efficiency.

300 μL steriled product flew through Vivapure D Mini H (ion exchange column), according to the manufacturer's instructions so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 11.

TABLE 11

A 260 value of liposome formulation F121

| Sample | $A_{260}$ value | $A_{260}$ average | siRNA Con. (mg/mL) |
|---|---|---|---|
| Incubation product | 0.2255<br>0.2203<br>0.2421 | 0.2314<br>0.2282<br>0.2434 | 0.2318 | 0.4171 |
| Sample before chromatography | 0.1966<br>0.1846<br>0.1912 | 0.1965<br>0.1932<br>0.1887 | 0.1918 | 0.7557 |
| Sample after chromatography | 0.0719<br>0.0728<br>0.0657 | 0.0686<br>0.0746<br>0.0673 | 0.0702 | 0.2764 |

3) Calculation of the encapsulation efficiency.

As described in Example 10, the actual concentration coefficient was calculated to be 49.07. Based on this coefficient, the actual siRNA concentration of the incubation product, the samples before chromatography, and the samples after chromatography were calculated and presented in Table 11. Based on the concentrations of the siRNA, the encapsulation efficiency was calculated to be 36.6%, and the concentration of ApoB-siRNA was calculated to be 0.2764 mg/mL in liposome formulation.

2.4.4 pKa measurement of the PFVs.

As described in Example 10, pKa of the PFVs was measured to be 7.45.

2.4.5 Particle size measurement.

With a Nicomp 370 particle sizing system, the sizes of the pre-formed empty vesicles and the siRNA liposome formulation were determined to be 58.90 nm and 68.03 nm, respectively.

EXAMPLE 14

Preparation of Liposome Formulation F122

1. Reagents, Materials, and Instruments 1.1 Reagents.

1.1.1 Lipids: the first cationic lipid, CL01, prepared in Example 5; the second cationic lipid, CL08, prepared in Example 7; phospholipids, DSPC, purchased from Shanghai Advanced Vehicle Technology Corporation; long-circulating lipid, PEG-DLM, prepared in Example 2.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:   5'-GUCAUCACACUGAAUACCAAU-3' (SEQ ID NO: 1);

ApB-AS:  5'-AUUGGUAUUCAGUGUGAUGACAC-3'
         (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation 2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, for measuring the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260}$×50 g/mL per OD×2000/1000=38.51 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 12. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NL1 liposome extruder. These procedures resulted in uniform PFV particles, whose sizes were determined using a particle sizing system.

TABLE 12

The component amounts for F122 formulation
Total Volume: 4.0 mL
Volume of ethanol: 1.2 mL, concentration of ethanol: 30% (v/v)

| Lipid | Concentration (mg/mL) | Amount (mL) |
|---|---|---|
| CL-01 | 40 | 0.150 |
| DSPC | 20 | 0.092 |
| CL08 | 20 | 0.221 |
| PEG-DLM | 50 | 0.121 |
| Ethanol further added | | 0.016 mL |

2.4.2 Preparation of siRNA liposome formulation.

PFV of desired volume was dispensed in a 50 mL Falcon tubes, pre-equilibrated in a 35° C. water bath for 4-5 min. 52 µL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 µL incubation product was used for $A_{260}$ measurement. The resulted liposome formulation was dialyzed overnight in 1×PBS, using a MD24 dialysis bag. The dialyzed product was then recovered, filtered sterilization using a 0.2 µm syringe filter. 600 µL of the product was measured for its encapsulation efficiency.

2.4.3 Measurement of encapsulation efficiency.

300 µL steriled product flew through Vivapure D Mini H (ion exchange column), according to the manufacturer's instructions, so as to perform a separation procedure. The resulted product was the sample after chromatography. The remaining original sample of 300 µL was the sample before chromatography.

1) According to Table 3, the samples for OD measurement ($A_{260}$) were prepared.
2) The absorbance at 260 nm wavelength was determined, using an ultraviolet spectrophotometer (n=3, two parallel measurements were performed for each sample). The results are shown in Table 13.

TABLE 13

A260 value of liposome formulation F122

| Sample | $A_{260}$ value | | $A_{260}$ average | siRNA Con. (mg/mL) |
|---|---|---|---|---|
| Incubation product | 0.2837 | 0.2922 | 0.3010 | 0.4576 |
| | 0.3020 | 0.3128 | | |
| | 0.3060 | 0.3093 | | |
| Sample before chromatography | 0.2127 | 0.2159 | 0.2277 | 0.2597 |
| | 0.2355 | 0.2365 | | |
| | 0.2365 | 0.2293 | | |
| Sample after chromatography | 0.1669 | 0.1583 | 0.1628 | 0.1856 |
| | 0.1639 | 0.1635 | | |
| | 0.1598 | 0.1644 | | |

3) Calculation of the encapsulation efficiency.

As described in Example 10, the actual concentration coefficient was calculated to be 41.46. Based on this coefficient, the actual siRNA concentration of the incubation product, the samples before chromatography, and the samples after chromatography were calculated and presented in Table 13. Based on the concentrations of the siRNA, the encapsulation efficiency was calculated to be 71.5%, and the concentration of ApoB-siRNA was calculated to be 0.1856 mg/mL in liposome formulation.

2.4.4 pKa measurement of the PFVs.

As described in Example 10, pKa of the PFVs was measured to be 6.65.

2.4.5 Particle size measurement.

With a Nicomp 370 particle sizing system, the sizes of the pre-formed empty vesicles and the siRNA liposome formulation were determined to be 57.00 nm and 68.88 nm, respectively.

EXAMPLE 15

Preparation of liposome formulation F123

1. Reagents, Materials, and Instruments 1.1 Reagents.

1.1.1 Lipids: the first cationic lipid, CL01, prepared in Example 5; the second cationic lipid, CL08, prepared in Example 7; phospholipids, DSPC, purchased from Shanghai Advanced Vehicle Technology Corporation; long-circulating lipid, PEG-DMM, prepared in Example 3.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:  5'-GUCAUCACACUGAAUACCAAU-3' (SEQ ID NO: 1);

ApB-AS: 5'-AUUGGUAUUCAGUGUGAUGACAC-3'
        (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation.

2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, measured the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260} \times 50$ g/mL per OD$\times 2000/1000 = 38.51$ mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 14. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nucleopore Membrane Circles at room temperature, using a NLI liposome extruder. These procedures resulted in uniform PFV particles, whose sizes were determined using a particle sizing system.

TABLE 14

The component amounts for F123 formulation
Total volume: 2 mL
Volume of ethanol: 0.6 mL, concentration of ethanol: 30% (v/v)

| Lipid | Concentration (mg/mL) | Amount (mL) |
|---|---|---|
| CL-01 | 40 | 0.150 |
| DSPC | 20 | 0.092 |
| CL08 | 20 | 0.221 |
| PEG-DMM | 50 | 0.116 |
| ethanol further added | | 0.020 |

2.4.2 Preparation of liposome formulation.

PFV of desired volume was dispensed in a 50 mL Falcon tubes, pre-equilibrated in a 35° C. water bath for 4-5 min. 52 μL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 μl incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured its encapsulation efficiency.

2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 15.

TABLE 15

A260 value of liposome formulation F123

| Sample | $A_{260}$ value | $A_{260}$ average | siRNA Con. (mg/mL) |
|---|---|---|---|
| Incubation product | 0.2930 0.2980 0.2943 | 0.3013 0.2982 0.3021 | 0.2978 | 0.4576 |
| Sample before chromatography | 0.1836 0.1999 0.1942 | 0.1875 0.1995 0.2033 | 0.1947 | 0.2243 |
| Sample after chromatography | 0.1611 0.1768 0.1745 | 0.1715 0.1661 0.175 | 0.1708 | 0.1969 |

3) Calculation of the encapsulation efficiency.

As described in Example 10, the actual concentration coefficient was calculated to be 41.9. Based on this coefficient, the actual siRNA concentration of the incubation product, the samples before chromatography, and the samples after chromatography were calculated and presented in Table 15. Based on the concentrations of the siRNA, the encapsulation efficiency was calculated to be 87.8%, and the concentration of ApoB-siRNA was calculated to be 0.1969 mg/mL in liposome formulation.

2.4.4 pKa measurement of the PFVs.

As described in Example 10, pKa of the PFVs was measured to be 6.58.

2.4.5 Particle size measurement.

With a Nicomp 370 particle sizing system, the sizes of the pre-formed empty vesicles and the siRNA liposome formulation were determined to be 60.84 nm and 69.43 nm, respectively.

EXAMPLE 16

Preparation of Liposome Formulation F128

1. Reagents, Materials, and Instruments 1.1 Reagents.

1.1.1 Lipids: the first cationic lipid, CL01, prepared in Example 5; the second cationic lipid, CL06, prepared in Example 6; phospholipids, DSPC, purchased from Shanghai Advanced Vehicle Technology Corporation; long-circulating lipid, PEG-chol, prepared in Example 4.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:  5'-GUCAUCACACUGAAUACCAAU-3' (SEQ ID NO: 1);

ApB-AS: 5'-AUUGGUAUUCAGUGUGAUGACAC-3'
        (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation.

2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, measured the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260} \times 50$ g/mL per OD×2000/1000=38.51 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 16. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 16

The component amounts for F128 formulation
Total volume: 2 mL
Volume of ethanol: 0.6 mL, concentration of ethanol: 30% (v/v)

| Lipid | Concentration (mg/mL) | Amount (mL) |
| --- | --- | --- |
| CL-01 | 40 | 0.150 |
| DSPC | 20 | 0.092 |
| CL06 | 20 | 0.227 |
| PEG-chol | 50 | 0.112 |
| Ethanol further added | | 0.018 mL |

2.4.2 Preparation of siRNA liposome formulation.

PFV of desired volume was dispensed in a 50 mL Falcon tubes, pre-equilibrated in a 35° C. water bath for 4-5 min. 52 μL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min, After incubation, 600 μL incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured for its encapsulation efficiency.

2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 17.

TABLE 17

A260 value of liposome formulation F128

| Sample | $A_{260}$ value | | $A_{260}$ average | siRNA Con. (mg/mL) |
| --- | --- | --- | --- | --- |
| Incubation product | 0.2904 | 0.2796 | 0.2943 | 0.4576 |
| | 0.2987 | 0.2946 | | |
| | 0.3004 | 0.3023 | | |

TABLE 17-continued

A260 value of liposome formulation F128

| Sample | $A_{260}$ value | | $A_{260}$ average | siRNA Con. (mg/mL) |
|---|---|---|---|---|
| Sample before chromatography | 0.2021<br>0.2307<br>0.2244 | 0.2141<br>0.2299<br>0.2251 | 0.2211 | 0.2577 |
| Sample after chromatography | 0.1966<br>0.1945<br>0.2018 | 0.1965<br>0.1846<br>0.2103 | 0.1974 | 0.2301 |

3) Calculation of the encapsulation efficiency.

As described in Example 10, the actual concentration coefficient was calculated to be 42.40. Based on this coefficient, the actual siRNA concentration of the incubation product, the samples before chromatography, and the samples after chromatography were calculated and presented in Table 17. Based on the concentrations of the siRNA, the encapsulation efficiency was calculated to be 89.3%, and the concentration of ApoB-siRNA was calculated to be 0.2301 mg/mL in liposome formulation.

2.4.4 pKa measurement of the PFVs.

As described in Example 10, pKa of the PFVs was measured to be 7.56.

2.4.5 Particle size measurement.

With a Nicomp 370 particle sizing system, the sizes of the pre-formed empty vesicles and the liposome formulation were determined to be 84.01 nm and 67.52 nm, respectively.

EXAMPLE 17

Preparation of Liposome Formulation F129

1. Reagents, Materials, and Instruments 1.1 Reagents.

1.1.1 Lipids: the first cationic lipid, CL01, prepared in Example 5; the second cationic lipid, CL08, prepared in Example 7; phospholipids, DSPC, purchased from Shanghai Advanced Vehicle Technology Corporation; long-circulating lipid, PEG-chol, prepared in Example 4.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

```
ApB-S:   5'-GUCAUCACACUGAAUACCAAU-3' (SEQ ID NO: 1);

ApB-AS:  5'-AUUGGUAUUCAGUGUGAUGACAC-3'
             (SEQ ID NO: 2).
```

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation.

2.1.1 siRNA dissolving buffer (10 mM citric acid, 30 mM NaCl, pH6.0): prepared with RNase-free water or water for injection, and upon adjusting pH, filtered with 0.22 μm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, measured the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260} \times 50$ g/mL per OD×2000/1000=38.51 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 18. After all the lipids were completely dissolved, the obtained ethanol solution of lipid mixture was added into a formulation buffer under stirring, to a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 18

The component amounts for F129 formulation
Total volume: 2 mL
Volume of ethanol: 0.6 mL, concentration of ethanol: 30% (v/v)

| Lipid | Concentration (mg/mL) | Amount (mL) |
|---|---|---|
| CL-01 | 40 | 0.150 |
| DSPC | 20 | 0.092 |
| CL08 | 20 | 0.221 |

TABLE 18-continued

The component amounts for F129 formulation
Total volume: 2 mL
Volume of ethanol: 0.6 mL, concentration of ethanol: 30% (v/v)

| Lipid | Concentration (mg/mL) | Amount (mL) |
|---|---|---|
| PEG-chol | 50 | 0.112 |
| Ethanol further added | | 0.024 |

2.4.2 Preparation of liposome formulation.

PFV of desired volume was dispensed in a 50 mL Falcon tubes, pre-equilibrated in a 35° C. water bath for 4-5 min. 52 μL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 6004 incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured for its encapsulation efficiency.

2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 19.

TABLE 19

A260 value of liposome formulation F129

| Sample | $A_{260}$ value | | $A_{260}$ average | siRNA Con. (mg/mL) |
|---|---|---|---|---|
| Incubation product | 0.3141 | 0.3308 | 0.3110 | 0.4576 |
| | 0.2966 | 0.3087 | | |
| | 0.3034 | 0.3125 | | |
| Sample before chromatography | 0.2257 | 0.2344 | 0.2284 | 0.2520 |
| | 0.2353 | 0.2411 | | |
| | 0.2214 | 0.2124 | | |
| Sample after chromatography | 0.2166 | 0.2177 | 0.2243 | 0.2474 |
| | 0.2252 | 0.2308 | | |
| | 0.2273 | 0.2279 | | |

3) Calculation of the encapsulation efficiency.

As described in Example 10, the actual concentration coefficient was calculated to be 40.13. Based on this coefficient, the actual siRNA concentration of the incubation product, the samples before chromatography, and the samples after chromatography were calculated and presented in Table 19. Based on the concentrations of the siRNA, the encapsulation efficiency was calculated to be 98.2%, and the concentration of ApoB-siRNA was calculated to be 0.2474 mg/mL in liposome formulation.

2.4.4 pKa measurement of the PFVs.

As described in Example 10, pKa of the PFVs was measured to be 6.74.

2.4.5 Particle size measurement.

With a Nicomp 370 particle sizing system, the sizes of the pre-formed empty vesicles and the liposome formulation were determined to be 102.2 nm and 66.07 nm, respectively.

EXAMPLE 18

Function Validation of Liposome Formulations F113 and F115

1. Reagents, Materials, and Instruments 1.1 Reagents and Materials: liposome formulations F113 (Prepared in Example 9) and F115 (Prepared in Example 10), Sodium Chloride solution for injection (Shandong Kangning Pharmaceutical Co.), RISO™ RNA extraction reagent (Biomics Biotechnologies Co. Ltd), EzOmics™ One-Step qPCR kit (Biomics Biotechnologies Co. Ltd), 1 mL sterile syringe (Henan Shuguang Jianshi Medical Devices Corporation), Total cholesterol assay kit (Nanjing Jiancheng Corporation).

1.2 Experimental Animals: 4-6 weeks old ICR mice, female, 18-22 g, purchased from Nantong University, Center of Comparative Medicine.

1.3 Instruments: LightCycler 480 Real-Time PCR instrument (Roche, USA), UV-visible spectrophotometer UV759s (Shanghai Jingke Corporation).

2. Experimental Methods 2.1 Experimental groups: According to the body weights measured before the administration of liposome formulation, the mice were divided into three groups, F113 group, F115 group, and saline group. Administration of the liposome formulation was performed as the follows:

F113 group: the administration amount of F113 formulation was determined according to siRNA dosing of 3 mg/kg;

F115 group: the administration amount of F115 formulation was determined according to siRNA dosing of 3 mg/kg;

Saline group: injection of 300 μL of sodium chloride solution.

2.2 Administration of liposome formulation: Mice were fixed by means of a mice fixation device. An administration amount of lipid-siRNA formulation was calculated according to siRNA dosing of 3 mg/kg. Using a 1 mL sterile syringe, the determined amount of lipid-siRNA formulation was injected into mice, through the tail vein. The control group was injected with 300 μL of sodium chloride solution.

2.3 Measurement of serum total cholesterol levels of the mice

Body weights of the mice were determined at 48 h after administration of lipid-siRNA formulation. By means of removal of an eye ball, about 800 μL of blood was obtained from each mouse. After incubated at 4° C. for one hour, the blood was centrifuged at 3000 rpm for 10 min, to isolate mouse serum. According to the manufacture's instruction, 10 μL of the serum was taken for total cholesterol measurement, to measure the absorbance at 500 nm.

The content of cholesterol is calculated as: the content of cholesterol=($A_{500}$ value of the sample/$A_{500}$ value of the standard)×concentration of the standard (concentration of the standard: 200 mg/dL, 5.17 mM).

2.4 Measurement of ApoB mRNA level in mice liver using Real-time quantitative PCR (RT-qPCR).

48 h after administration of lipid-siRNA formulation, the mice were sacrificed. Three tissue samples were collected from different locations of mice liver. Total RNAs were extracted using RISO™ RNA kit, according to manufacturer's instruction. The expressional levels of ApoB gene were determined, using qRT-PCR.

Gene-specific primers were used to determine the mRNA expressional levels of ApoB gene in tissue sample. A housekeeping gene, GAPDH, was simultaneously amplified and used as an internal reference. For each sample, TF gene and internal reference gene GAPDH were simultaneously amplified, each reaction in triplicate. Gene expressional levels were quantified using One-Step qPCR kit, the reaction system including: 2 μL of RNA template, 12.5 μL of 2×Master Mix, 0.5 μL of 5' end primer (10 μM) and 3' end primer (10 μM) each, 0.5 μL of 50×SYBR Green I Solution, RNase-free water was added to make up the system to 25 μL. After mixing, the reaction system was placed on a real-time quantitative PCR instrument to perform the reaction.

Detection of ApoB mRNA: Sequence of the 5' end primer, 5'-AAGCACCTCCGAAAGTACGTG (SEQ ID NO:3); Sequence of the 3' end primer, 5'-CTCCAGCTCTACCT-TACAGTTGA (SEQ ID NO:4). Detection of housekeeping gene GAPDH: Sequence of the 5' end primer, 5'-GTAT-GACTCCACTCACGGCAAA (SEQ ID NO:5); Sequence of the 3' end primer, 5'-GGTCTCGCTCCTGGAAGATG (SEQ ID NO:6). All the primers were synthesized by Biomics Biotechnologies Co. Ltd.

Reaction conditions: reverse transcription at 42° C. for 30 min; pre-denaturation at 95° C. for 5 min; 45 PCR cycles were performed by denaturing at 95° C. for 20 sec, annealing at 58° C. for 30 sec, extending at 72° C. for 30 sec. The dissolution profiles of the reaction were determined as: 95° C./5 min, 58° C./5 min, increased the temperature to 95° C. at a speed of 0.5° C./5 sec.

2.5 Statistic Analysis

Statistic analysis was performed using SPSS 14.0 statistical software. Measurement data were presented as x̄±s, the significant differences among multiple groups were tested using single-factor analysis of variance, the significant differences between two groups were tested using t-test, $P<0.05$ indicates significant difference.

3. Experimental Results 3.1 The changes of mice body weights. Body weights were measured before and after administration of a liposome formulation. The changes of mice body weights can be used as an indirect index for the toxicity of the liposome formulation. As shown in FIG. 1, no significant change of mice body weights was observed in each group, before and after administration of the liposome formulation. This indicated no significant toxicity of the liposome formulation in concerned.

Figure 2:
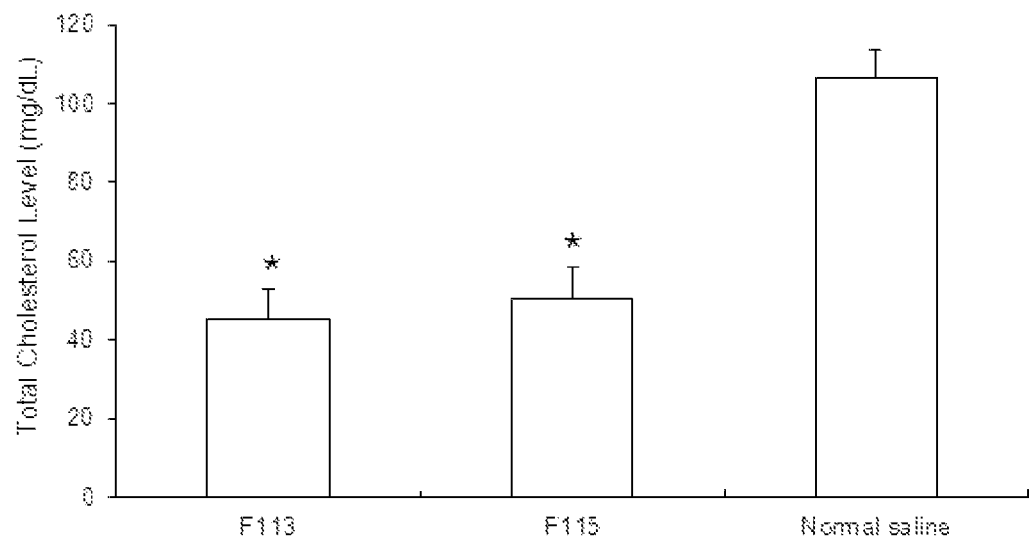
FIG. 2 is a bar graph depicting the serum total cholesterol levels of the mice before and after administration of liposome formulations F113 and F115. The horizontal axis represents the experimental groups and the vertical axis represents the serum total cholesterol levels.

3.2 The changes of the total cholesterol content were shown in FIG. 2. Compared to the control group, administration of liposome formulations F113 and F115 lowered serum total cholesterol levels (*$P<0.05$).

Figure 3:
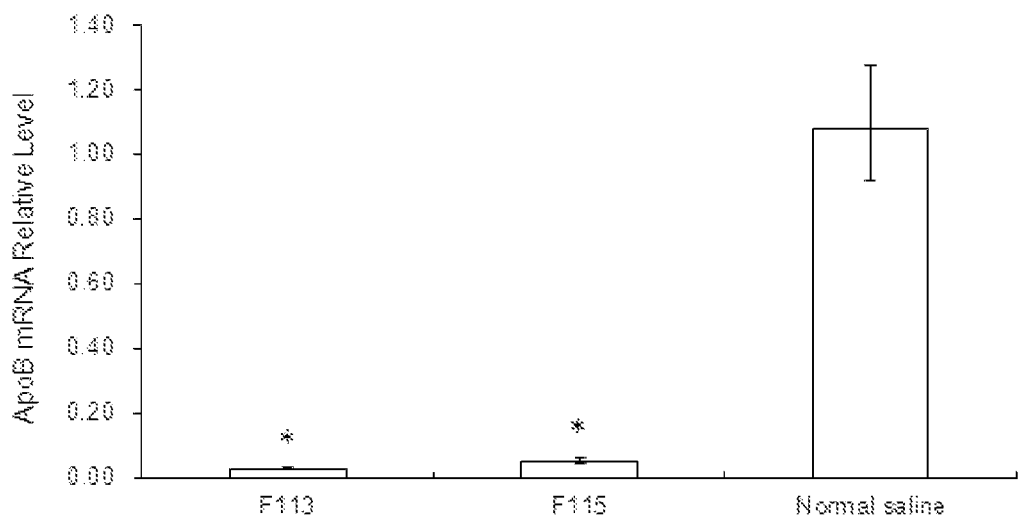
FIG. 3 is a bar graph depicting the relatively expressional levels of ApoB mRNA in mice liver after administration of liposome formulations F113 and F115. The horizontal axis represents the experimental groups and the vertical axis represents the relatively expressional levels of ApoB mRNA.

3.3 The changes of mRNA level of ApoB were shown in FIG. 3. Administration of liposome formulations F113 and F115 effectively inhibited the expression of ApoB mRNA in the liver (*$P<0.05$).

In summary, therapeutic nucleic acids, for example siRNAs, were successfully delivered to target tissues or organs by liposome formulations F113 and F115, and therapeutic nucleic acids can efficiently exhibit their functions.

EXAMPLE 19

Function Validation of Liposome Formulations F121, F123, F128 and F129

1. Reagents, Materials, and Instruments 1.1 Reagents and Materials: liposome formulations F121 (Prepared in Example 12), F123 (Prepared in Example 14), F129 (Prepared in Example 15) and F 129 (Prepared in Example 16), Sodium Chloride solution for injection (Shandong Kangning Pharmaceutical Co.), RISO™ RNA RNA extraction reagent (Biomics Biotechnologies Co. Ltd), EzOmics™ One-Step qPCR kit (Biomics Biotechnologies Co. Ltd), 1 mL sterile syringe (Henan Shuguang Jianshi medical Devices Corporation), Total cholesterol assay kit (Nanjing Jiancheng Corporation).

1.2 Experimental Animals: 4-6 weeks old ICR mice, female, 18-22 g, purchased from Nantong University, Center of Comparative Medicine.

1.3 Instruments: LightCycler 480 Real-Time PCR instrument (Roche, USA), UV-visible spectrophotometer UV759s (Shanghai Jingke Corporation).

2. Experimental Methods 2.1 Experimental groups: According to the body weights measured before the administration of liposome formulation, the mice were divided into five groups, F121 group, F123 group, F128 group, F129 group, and saline group. Administration of the liposome formulation was performed as the follows:

F121 group: the administration amount of F121 formulation was determined according to siRNA dosing of 3 mg/kg;

F123 group: the administration amount of F123 formulation was determined according to siRNA dosing of 3 mg/kg;

F128 group: the administration amount of F128 formulation was determined according to siRNA dosing of 3 mg/kg;

F129 group: the administration amount of F129 formulation was determined according to siRNA dosing of 3 mg/kg;

Saline group: injection of 300 μL of sodium chloride solution.

2.2 Administration of liposome formulation: Mice were fixed by means of a mice fixation device. An administration amount of siRNA liposome formulation was calculated according to siRNA dosing of 3 mg/kg. Using a 1 mL sterile syringe, the determined amount of lipid-siRNA formulation was injected into mice, through the tail vein. The control group was injected with 300 μL of sodium chloride solution.

2.3 Measurement of serum total cholesterol levels of the mice 48 h after administration of lipid-siRNA formulation, body weights of the mice were determined. By means of removal of an eye ball, about 800 μL of blood was obtained from each mouse. After incubated at 4° C. for one hour, the blood was centrifuged at 3000 rpm for 10 min, to isolate mouse serum. According to the manufacture's instruction, 10 μL of the serum was taken for total cholesterol measurement to measure the absorbance at 500 nm.

The content of cholesterol is calculated as: the content of cholesterol=($A_{500}$ value of the sample/$A_{500}$ value of the standard)×concentration of the standard (concentration of the standard: 200 mg/dL, 5.17 mM).

2.4 Measurement of ApoB mRNA level in mice liver using Real-time quantitative PCR.

48 h after administration of lipid-siRNA formulation, the mice were sacrificed. Three tissue samples were collected from different locations of mice liver. Total RNAs were extracted using RISO™ RNA kit, according to manufacturer's instruction. The mRNA expressional levels of ApoB gene were determined, using qRT-PCR.

Gene-specific primers were used to determine the mRNA expressional levels of ApoB gene in tissue sample. A housekeeping gene, GAPDH, was simultaneously amplified and used as an internal reference. For each sample, TF gene and internal reference gene GAPDH were simultaneously amplified, each reaction in triplicate. Gene expressional levels were quantified using One-Step qPCR kit, the reaction system including: 2 μL of RNA template, 12.5 μL of 2×Master Mix, 0.5 μL of 5' end primer (10 μM) and 3' end primer (10 μM) each, 0.5 μL of 50×SYBR Green I Solution, RNase-free water was added to make up the system to 25 μL. After mixing, the reaction system was placed on a real-time quantitative PCR instrument to perform the reaction.

Detection of ApoB mRNA: Sequence of the 5' end primer, 5'-AAGCACCTCCGAAAGTACGTG (SEQ ID NO:3); Sequence of the 3' end primer, 5'-CTCCAGCTCTACCT-TACAGTTGA (SEQ ID NO:4). Detection of housekeeping gene GAPDH: Sequence of the 5' end primer, 5'-GTAT-GACTCCACTCACGGCAAA (SEQ ID NO:5); Sequence of the 3' end primer, 5'-GGTCTCGCTCCTGGAAGATG (SEQ ID NO:6). All the primers were synthesized by Biomics Biotechnologies Co. Ltd.

Reaction conditions: reverse transcription at 42° C. for 30 min; pre-denaturation at 95° C. for 5 min; 45 PCR cycles were performed by denaturing at 95° C. for 20 sec, annealing at 58° C. for 30 sec, extending at 72° C. for 30 sec. The dissolution profiles of the reaction were determined as: 95° C./5 min, 58° C./5 min, increased the temperature to 95° C. at a speed of 0.5° C./5 sec.

2.5 Statistic analysis

Statistic analysis was performed using SPSS 14.0 statistical software. Measurement data were presented as $\bar{x}\pm s$, the significant differences among multiple groups were tested using single-factor analysis of variance, the significant differences between two groups were tested using t-test, P<0.05 indicates significant difference.

Figure 4:
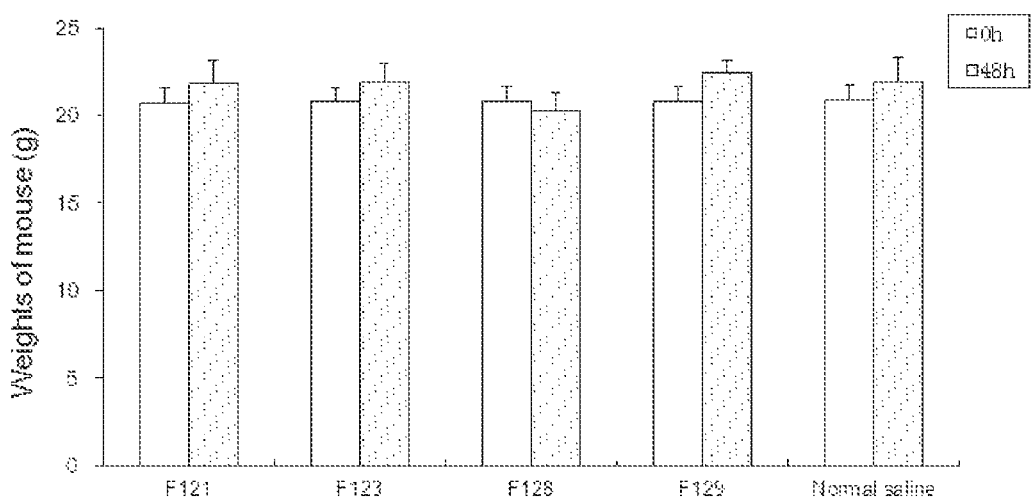
FIG. 4 is a bar graph depicting the body weights of the mice before and after administration of liposome formulations F121, F123, F128 and F129. The horizontal axis represents the experimental groups and the vertical axis represents the body weights of the mice.

3. Experimental Results 3.1 The changes of mice body weights. Body weights were measured before and after administration of a liposome formulation. The changes of mice body weights can be used as an indirect index for the toxicity of the liposome formulation. As shown in FIG. 4, no significant change of mice body weights was observed in each group, before and after administration of the liposome formulation. This indicated no significant toxicity of the liposome formulation in concerned.

Figure 5:
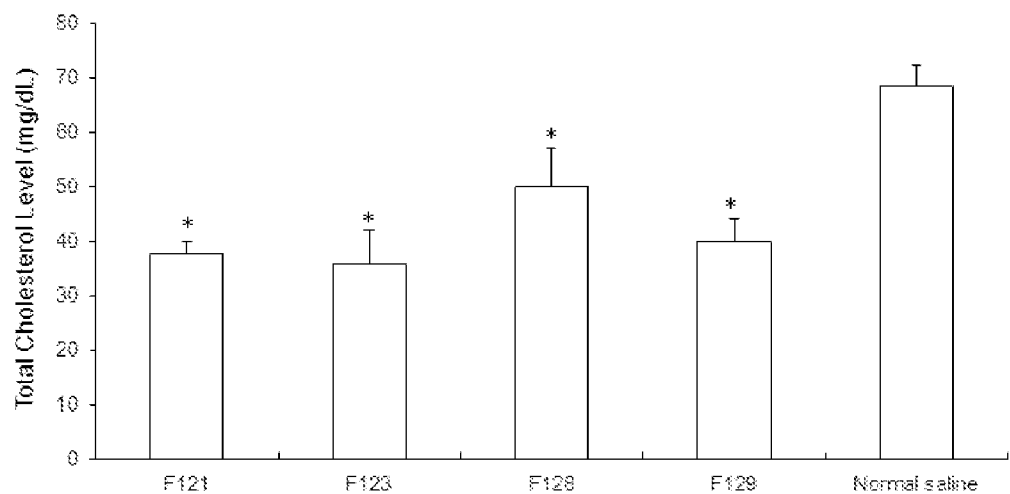
FIG. 5 is a bar graph depicting the serum total cholesterol levels of the mice after administration of liposome formulations F121, F123, F128 and F129. The horizontal axis represents the experimental groups and the vertical axis represents the serum total cholesterol levels of the mice.

3.2 The changes of the total cholesterol content were shown in FIG. 5. Compared to the control group, administration of liposome formulations F121, F123, F128 and F129 lowered serum total cholesterol levels (*P<0.05).

Figure 6:
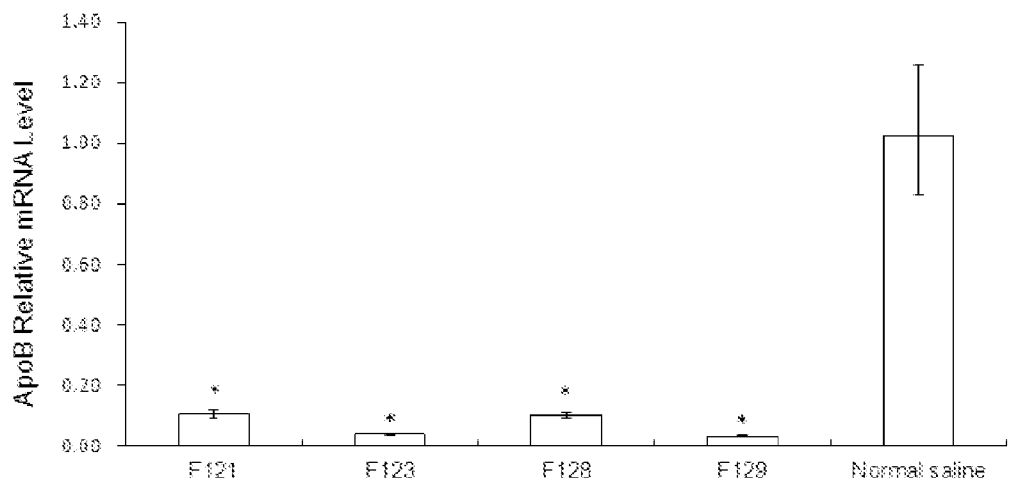
FIG. 6 is a bar graph depicting the relatively expressional levels of ApoB mRNA in mice liver after administration of liposome formulations F121, F123, F128 and F129. The horizontal axis represents the experimental groups and the vertical axis represents the relatively expressional levels of ApoB mRNA.

3.3 The changes of mRNA level of ApoB were shown in FIG. 6. Administration of liposome formulations F121, F123, F128 and F129 effectively inhibited the expression of ApoB mRNA in the liver (*P<0.05).

In summary, therapeutic nucleic acids, for example siRNAs, were successfully delivered to target tissues or organs by liposome formulations F121, F123, F128 and F129, and the therapeutic nucleic acids can efficiently exhibit their functions.

EXAMPLE 20

Function Validation of Liposome Formulations F120 and F122

1. Reagents, materials, and instruments.

1.1 Reagents and Materials: liposome formulations F120 (Prepared in Example 12) and F122 (Prepared in Example 14), Sodium Chloride solution for injection (Shandong Kangning Pharmaceutical Co.), RISO™ RNA RNA extraction reagent (Biomics Biotechnologies Co. Ltd), EzOmics™ One-Step qPCR kit (Biomics Biotechnologies Co. Ltd), 1 mL sterile syringe (Henan Shuguang Jianshi medical Devices Corporation), Total cholesterol assay kit (Nanjing Jiancheng Corporation).

1.2 Experimental Animals: 4-6 weeks old ICR mice, female, 18-22 g, purchased from Nantong University, Center of Comparative Medicine.

1.3 Instruments: LightCycler 480 Real-Time PCR instrument (Roche, USA), UV-visible spectrophotometer UV759s (Shanghai Jingke Corporation).

2. Experimental Methods 2.1 Experimental groups: According to the body weights measured before the administration of liposome formulation, the mice were divided into three groups, F120 group, F122 group, and saline group. Administration of the liposome formulation was performed as the follows:

F120 group: the administration amount of F120 formulation was determined according to siRNA dosing of 3 mg/kg;

F122 group: the administration amount of F122 formulation was determined according to siRNA dosing of 3 mg/kg;

Saline group: injection of 300 μL of sodium chloride solution.

2.2 Administration of liposome formulation: Mice were fixed by means of a mice fixation device. An administration amount of liposome formulation was calculated according to siRNA dosing of 3 mg/kg. Using a 1 mL sterile syringe, the determined amount of liposome formulation was injected into mice, through the tail vein. The control group was injected with 300 μL of sodium chloride solution.

2.3 Measurement of serum total cholesterol levels of the mice 48 h after administration of lipid-siRNA formulation, body weights of the mice were determined. By means of removal of an eye ball, about 800 μL of blood was obtained from each mouse. After incubated at 4° C. for one hour, the blood was centrifuged at 3000 rpm for 10 min, to isolate mouse serum. 10 μL of the serum was taken for total cholesterol measurement, according to the manufacture's instruction to measure the absorbance at 500 nm.

The content of cholesterol is calculated as: the content of cholesterol=($A_{500}$ value of the sample/$A_{500}$ value of the standard)×concentration of the standard (concentration of the standard: 200 mg/dL, 5.17 mM).

2.4 Measurement of ApoB mRNA level in mice liver using Real-time quantitative PCR.

48 h after administration of lipid-siRNA formulation, the mice were sacrificed. Three tissue samples were collected from different locations of mice liver. Total RNAs were extracted using RISO™ RNA kit, according to manufacturer's instruction. The mRNA expressional levels of ApoB gene were determined, using qRT-PCR.

Gene-specific primers were used to determine the mRNA expressional levels of ApoB gene in tissue sample. A housekeeping gene, GAPDH, was simultaneously amplified and used as an internal reference. For each sample, TF gene and internal reference gene GAPDH were simultaneously amplified, each reaction in triplicate. Gene expressional levels were quantified using One-Step qPCR kit, the reaction system including: 2 μL of RNA template, 12.5 μL of 2×Master Mix, 0.5 μL of 5' end primer (10 μM) and 3' end primer (10 μM) each, 0.5 μL of 50×SYBR Green I Solution, RNase-free water was added to make up the system to 25 μL. After mixing, the reaction system was placed on a real-time quantitative PCR instrument to perform the reaction.

Detection of ApoB mRNA: Sequence of the 5' end primer, 5'-AAGCACCTCCGAAAGTACGTG (SEQ ID NO:3); Sequence of the 3' end primer, 5'-CTCCAGCTCTACCT-TACAGTTGA (SEQ ID NO:4). Detection of housekeeping gene GAPDH: Sequence of the 5' end primer, 5'-GTAT-GACTCCACTCACGGCAAA (SEQ ID NO:5); Sequence of the 3' end primer, 5'-GGTCTCGCTCCTGGAAGATG (SEQ ID NO:6). All the primers were synthesized by Biomics Biotechnologies Co. Ltd.

Reaction conditions: reverse transcription at 42° C. for 30 min; pre-denaturation at 95° C. for 5 min; 45 PCR cycles were performed by denaturing at 95° C. for 20 sec, annealing at 58° C. for 30 sec, extension at 72° C. for 30 sec. The dissolution profiles of the reaction were determined as: 95° C./5 min, 58° C./5 min, increased the temperature to 95° C. at a speed of 0.5° C./5 sec.

2.5 Statistic analysis

Statistic analysis was performed using SPSS 14.0 statistical software. Measurement data were presented as x̄±s, the significant differences among multiple groups were tested using single-factor analysis of variance, the significant differences between two groups were tested using t-test, P<0.05 indicates significant difference.

Figure 7:
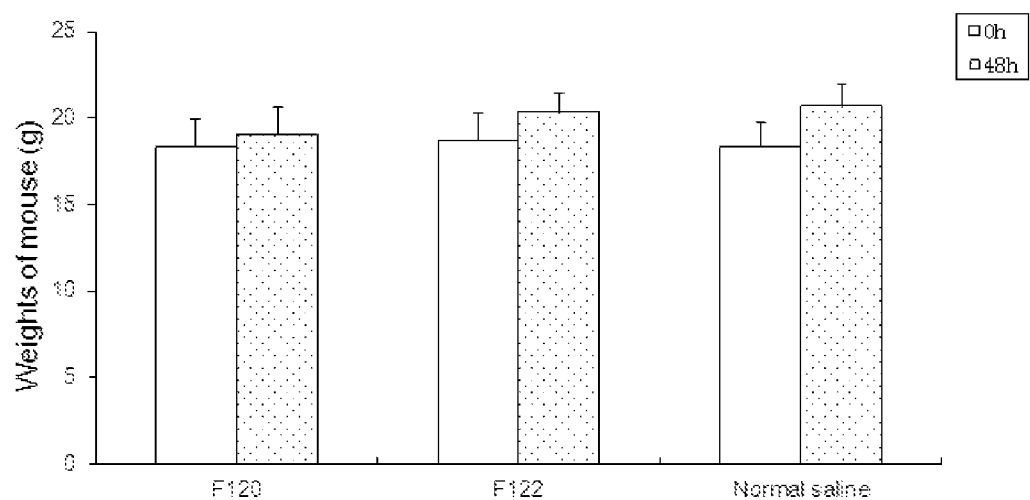
FIG. 7 is a bar graph depicting the body weights of the mice before and after administration of liposome formulations F120 and F122. The horizontal axis represents the experimental groups and the vertical axis represents the body weights of the mice.

3. Experimental Results 3.1 The changes of mice body weights. Mice body weights were measured before and after administration of a liposome formulation. The changes of mice body weights can be used as an indirect index for the toxicity of the liposome formulation. As shown in FIG. 7, no significant change of mice body weights was observed in each group, before and after administration of the liposome formulation. This indicated no significant toxicity of the liposome formulation in concerned.

Figure 8:
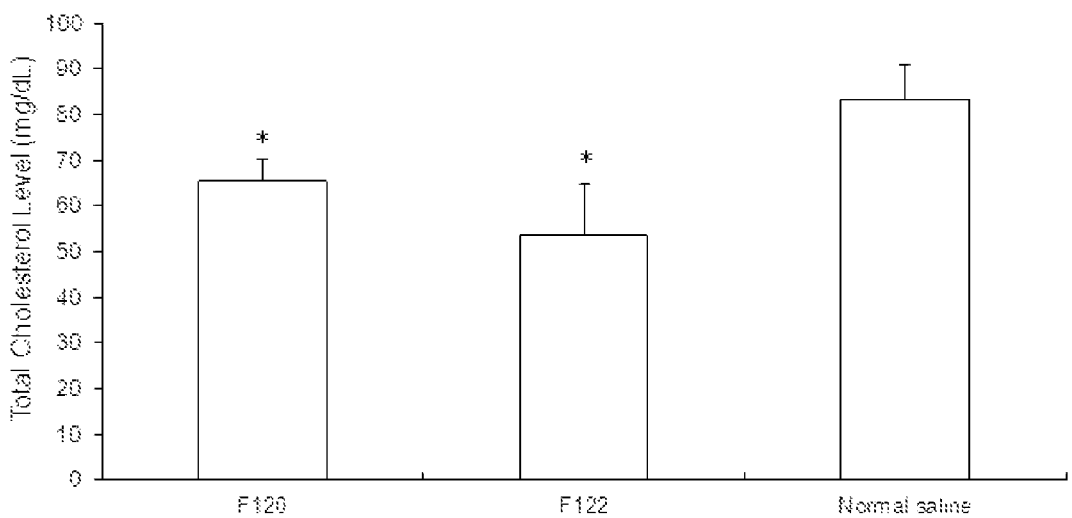
FIG. 8 is a bar graph depicting the serum total cholesterol levels of the mice after administration of liposome formulations F120 and F122. The horizontal axis represents the experimental groups and the vertical axis represents the serum total cholesterol levels of the mice.

3.2 The changes of the total cholesterol content were shown in FIG. 8. Compared to the control group, administration of liposome formulations F120 and F122 lowered serum total cholesterol levels (*P<0.05).

Figure 9:
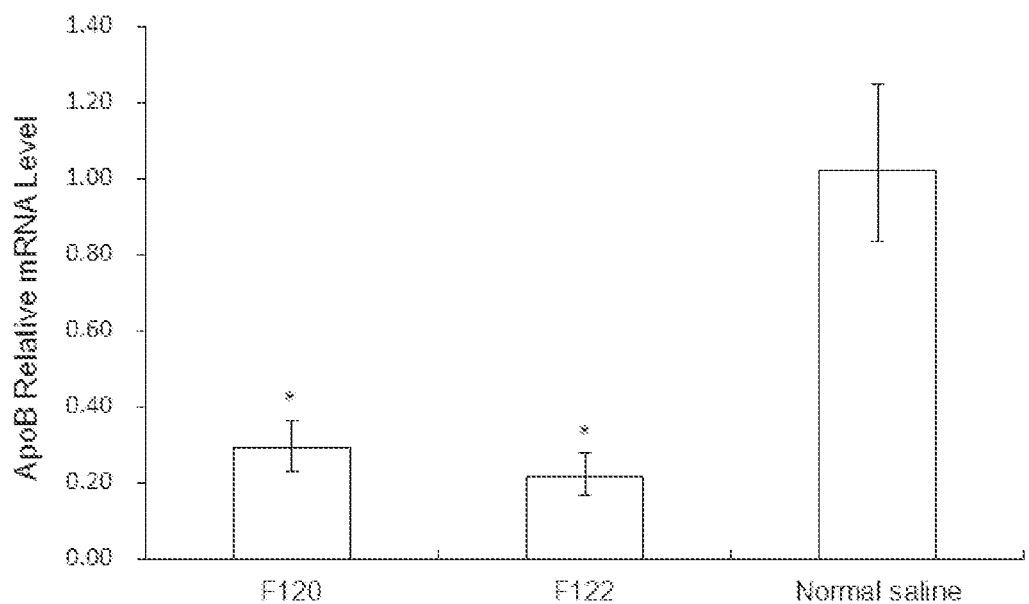
FIG. 9 is a bar graph depicting the relatively expressional levels of ApoB mRNA in mice liver after administration of liposome formulations F120 and F122. The horizontal axis represents the experimental groups and the vertical axis represents the relatively expressional levels of ApoB mRNA in mice liver.

3.3 The changes of mRNA level of ApoB were shown in FIG. 9. Administration of liposome formulations F120 and F122 effectively inhibited the expression of ApoB mRNA in the liver (*P<0.05).

In summary, therapeutic nucleic acids, for example siRNAs, were successfully delivered to target tissues or organs by liposome formulations F120 and F122, and therapeutic nucleic acids can efficiently exhibit their functions.

EXAMPLE 21

Preparation of Liposome Formulation F157
1. Reagents, materials, and instruments.
1.1 Reagents.
1.1.1 Lipids: the first cationic lipid, DLinDMA, prepared in Example 8; the second cationic lipid, CL08, prepared in Example 7; phospholipids, DSPC, purchased from Shanghai Advanced Vehicle Technology Corporation; long-circulating lipid, PEG-c-DMA, prepared in Example 9.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:  5'-GUCAUCACACUGAAUACCAAU-3' (SEQ ID NO: 1);

ApB-AS: 5'-AUUGGUAUUCAGUGUGAUGACAC-3'
        (SEQ ID NO: 1).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation.
2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.
2.1.2 Formulation buffer (50 mM citric acid, pH4.0): prepared as described in 2.1.1.
2.1.3 Dialysis buffer: 1×phosphate buffer (phosphate-buffered saline, PBS) (Biomics Biotechnologies Co. Ltd).
2.2 Preparation of siRNA stock solution.
2.2.1 siRNA dissolvation: ApoB-siRNA stock solution of 50 mg/mL was prepared with solution of 10 mM citrate/30 mM NaCl, pH6.0.
2.2.2 An aliquot of ApoB-siRNA stock solution was diluted in 2000-fold with PBS, measured the concentration of the siRNA. Three parallel measurements were performed for each sample.
2.2.3 Using a UV spectrophotometer, $A_{260}$ value was measured and the actual concentration of ApoB-siRNA in the stock solution was determined. As shown in Table 7, $A_{260}$×50 g/mL per OD×2000/1000=38.51 mg/mL.
2.3 Preparation of lipid storage solution.
2.3.1 Before measurement, the first cationic lipid, the second cationic lipid, phospholipid and long-circulating lipid were pre-equilibrated for about 30 min at room temperature.
2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 20. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 20

The component amounts for F157 formulation
Total volume: 4 mL
Volume of ethanol: 1.2 mL, concentration of ethanol: 30% (v/v)

| Lipid | Concentration (mg/mL) | Amount (mL) |
|---|---|---|
| DLinDMA | 40 | 0.275 |
| DSPC | 20 | 0.176 |
| CL08 | 20 | 0.421 |
| PEG-c-DMA | 50 | 0.228 |
| Ethanol further added | | 0.100 mL |

2.4.2 Preparation of siRNA liposome formulation.

PFV of desired volume was dispensed in a 50 mL Falcon tubes, pre-equilibrated in a 35° C. water bath for 4-5 min. 52 µL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 µL incubation product was used for $A_{260}$ measurement. The resulted liposome formulation was dialyzed overnight in 1×PBS, using a MD24 dialysis bag. The dialyzed product was then recovered, filtered sterilization using a 0.2 µm syringe filter. 600 µL of the product was measured for its encapsulation efficiency.

2.4.3 Measurement of encapsulation efficiency.

300 µL steriled product flew through Vivapure D Mini H (ion exchange column), according to the manufacturer's instructions so as to perform a separation procedure. The resulted product was the sample after chromatography. The remaining original sample of 300 µL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 21.

TABLE 21

A260 value of liposome formulation F157

| Sample | $A_{260}$ value | $A_{260}$ average | | siRNA Con. (mg/mL) |
|---|---|---|---|---|
| Incubation product | 0.3521 | 0.3557 | 0.3497 | 0.4331 |
| | 0.3434 | 0.3477 | | |
| | 0.3474 | 0.3518 | | |
| Sample before chromatography | 0.2486 | 0.2494 | 0.2507 | 0.2329 |
| | 0.2484 | 0.2494 | | |
| | 0.2521 | 0.2562 | | |
| Sample after chromatography | 0.1717 | 0.1663 | 0.1665 | 0.1546 |
| | 0.1618 | 0.1664 | | |
| | 0.1623 | 0.1702 | | |

3) Calculation of the encapsulation efficiency.

As described in Example 10, the actual concentration coefficient was calculated to be 33.78. Based on this coefficient, the actual siRNA concentration of the incubation product, the samples before chromatography, and the samples after chromatography were calculated and presented in Table 21. Based on the concentrations of the siRNA, the encapsulation efficiency was calculated to be 66.4%, and the concentration of ApoB-siRNA was calculated to be 0.155 mg/mL in liposome formulation.

2.4.4 pKa measurement of the PFVs.

As described in Example 10, pKa of the PFVs was measured to be 5.97.

2.4.5 Particle size measurement.

With a Nicomp 370 particle sizing system, the sizes of the pre-formed empty vesicles and the liposome-nucleic acid formulation were determined to be 74.00 nm and 66.29 nm, respectively.

EXAMPLE 22

Preparation of Liposome Formulation F159

1. Reagents, materials, and instruments.

1.1 Reagents.

1.1.1 Lipids: the first cationic lipid, DLinDMA, prepared in Example 8; the second cationic lipid, CL08, prepared in Example 7; phospholipids, DSPC, purchased from Shanghai Advanced Vehicle Technology Corporation; long-circulating lipid, PEG-DMM, prepared in Example 3.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:  5'-GUCAUCACACUGAAUACCAAU-3' (SEQ ID NO: 1);

ApB-AS: 5'-AUUGGUAUUCAGUGUGAUGACAC-3'
        (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation.

2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.

2.1.2 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, measured the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260} \times 50$ g/mL per OD×2000/1000=38.51 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 22. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 22

The component amounts for F159 formulation
Total volume: 4 mL
Volume of ethanol: 1.2 mL, concentration of ethanol: 30% (v/v)

| Lipid | Concentration (mg/mL) | Amount (mL) |
|---|---|---|
| DLinDMA | 40 | 0.275 |
| DSPC | 20 | 0.176 |
| CL08 | 20 | 0.421 |

TABLE 22-continued

The component amounts for F159 formulation
Total volume: 4 mL
Volume of ethanol: 1.2 mL, concentration of ethanol: 30% (v/v)

| Lipid | Concentration (mg/mL) | Amount (mL) |
|---|---|---|
| PEG-DMM | 50 | 0.222 |
| Ethanol further added | | 0.105 |

2.4.2 Preparation of liposome formulation.

PFV of desired volume was dispensed in a 50 mL Falcon tubes, pre-equilibrated in a 35° C. water bath for 4-5 min. 52 μL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 μL incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured for its encapsulation efficiency.

2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 23.

TABLE 23

A260 value of liposome formulation F159

| Sample | $A_{260}$ value | | $A_{260}$ average | siRNA Con. (mg/mL) |
|---|---|---|---|---|
| Incubation product | 0.2953 | 0.2983 | 0.2996 | 0.4331 |
|  | 0.2936 | 0.2975 | | |
|  | 0.3014 | 0.3115 | | |
| Sample before chromatography | 0.2668 | 0.2651 | 0.2609 | 0.2828 |
|  | 0.2521 | 0.2608 | | |
|  | 0.2571 | 0.2633 | | |
| Sample after chromatography | 0.1663 | 0.1712 | 0.1684 | 0.1826 |
|  | 0.1614 | 0.164 | | |
|  | 0.1714 | 0.1761 | | |

3) Calculation of the encapsulation efficiency.

As described in Example 10, the actual concentration coefficient was calculated to be 39.43. Based on this coefficient, the actual siRNA concentration of the incubation product, the samples before chromatography, and the samples after chromatography were calculated and presented in Table 23. Based on the concentrations of the siRNA, the encapsulation efficiency was calculated to be 64.6%, and the concentration of ApoB-siRNA was calculated to be 0.183 mg/mL in liposome formulation.

2.4.4 pKa measurement of the PFVs.

As described in Example 10, pKa of the PFVs was measured to be 6.01.

2.4.5 Particle size measurement.

With a Nicomp 370 particle sizing system, the sizes of the pre-formed empty vesicles and the liposome-nucleic acid formulation were determined to be 74.25 nm and 65.01 nm, respectively.

EXAMPLE 23

Preparation of Liposome Formulation F165
1. Reagents, materials, and instruments.
1.1 Reagents.
1.1.1 Lipids: the first cationic lipid, DLinDMA, prepared in Example 8; the second cationic lipid, CL06, prepared in Example 6; phospholipids, DSPC, purchased from Shanghai Advanced Vehicle Technology Corporation; long-circulating lipid, PEG-c-DMA, prepared in Example 9.
1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.
1.2 ApoB-siRNA, synthesized by Biomics Biotechnologies Co. Ltd and provided as a freeze-dried powder. Sequences of the siRNA are:

```
ApB-S:    5'-GUCAUCACACUGAAUACCAAU-3' (SEQ ID NO: 1);

ApB-AS:   5'-AUUGGUAUUCAGUGUGAUGACAC-3'
          (SEQ ID NO: 2).
```

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome formulation.
2.1 Reagent preparation.
2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.
2.1.2 Formulation buffer (50 mM citric acid, pH4.0): prepared as described in 2.1.1.
2.1.3 Dialysis buffer: 1×phosphate buffer (phosphate-buffered saline, PBS) (Biomics Biotechnologies Co. Ltd).
2.2 Preparation of siRNA stock solution.
2.2.1 siRNA dissolvation: ApoB-siRNA stock solution of 50 mg/mL was prepared with solution of 10 mM citrate/30 mM NaCl, pH6.0.
2.2.2 An aliquot of ApoB-siRNA stock solution was diluted in 2000-fold with PBS, measured the concentration of the siRNA. Three parallel measurements were performed for each sample.

2.2.3 Using a UV spectrophotometer, $A_{260}$ value was measured and the actual concentration of ApoB-siRNA in the stock solution was determined. As shown in Table 7, $A_{260} \times 50$ g/mL per OD×2000/1000=38.51 mg/mL.

2.3 Preparation of lipid storage solution.
2.3.1 Before measurement, the first cationic lipid, the second cationic lipid, phospholipid and long-circulating lipid were pre-equilibrated for about 30 min at room temperature.
2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.
2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 24. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 24

The component amounts for F165 formulation
Total volume: 4 mL
Volume of ethanol: 1.2 mL, concentration of ethanol: 30% (v/v)

| Lipid | Concentration (mg/mL) | Amount (mL) |
|---|---|---|
| DLinDMA | 40 | 0.275 |
| DSPC | 20 | 0.176 |
| CL06 | 20 | 0.434 |
| PEG-c-DMA | 50 | 0.228 |
| Ethanol further added | | 0.087 mL |

2.4.2 Preparation of siRNA liposome formulation.

PFV of desired volume was dispensed in a 50 mL Falcon tubes, pre-equilibrated in a 35° C. water bath for 4-5 min. 52 μl ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 μL incubation product was used for $A_{260}$ measurement. The resulted liposome formulation was dialyzed overnight in 1×PBS, using a MD24 dialysis bag. The dialyzed product was then recovered, filtered sterilization using a 0.2 syringe filter. 600 μL of the product was measured for its encapsulation efficiency.

2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 25.

TABLE 25

A260 value of liposome formulation F165

| Sample | $A_{260}$ value | | $A_{260}$ average | siRNA Con. (mg/mL) |
|---|---|---|---|---|
| Incubation product | 0.3206 | 0.3263 | 0.3197 | 0.4331 |
|  | 0.3179 | 0.3223 |  |  |
|  | 0.3157 | 0.3153 |  |  |
| Sample before chromatography | 0.2320 | 0.2292 | 0.2235 | 0.2271 |
|  | 0.2197 | 0.2213 |  |  |
|  | 0.2193 | 0.2194 |  |  |
| Sample after chromatography | 0.1344 | 0.1286 | 0.1328 | 0.1350 |
|  | 0.1367 | 0.1406 |  |  |
|  | 0.1282 | 0.1285 |  |  |

3) Calculation of the encapsulation efficiency.

As described in Example 10, the actual concentration coefficient was calculated to be 36.95. Based on this coefficient, the actual siRNA concentration of the incubation product, the samples before chromatography, and the samples after chromatography were calculated and presented in Table 25. Based on the concentrations of the siRNA, the encapsulation efficiency was calculated to be 59.4%, and the concentration of ApoB-siRNA was calculated to be 0.3375 mg/mL in liposome formulation.

2.4.4 pKa measurement of the PFVs.

As described in Example 10, pKa of the PFVs was measured to be 6.87.

2.4.5 Particle size measurement.

With a Nicomp 370 particle sizing system, the sizes of the pre-formed empty vesicles and the liposome-nucleic acid formulation were determined to be 71.72 nm and 64.39 nm, respectively.

EXAMPLE 24

Preparation of Liposome Formulation F167
1. Reagents, materials, and instruments.
1.1 Reagents.
1.1.1 Lipids: the first cationic lipid, DLinDMA, prepared in Example 8; the second cationic lipid, CL06, prepared in Example 6; phospholipids, DSPC, purchased from Shanghai Advanced Vehicle Technology Corporation; long-circulating lipid, PEG-DMM, prepared in Example 3.
1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.
1.2 ApoB-siRNA, synthesized by Biomics Biotechnologies Co. Ltd and provided as a freeze-dried powder. Sequences of the siRNA are:

ApB-S:   5'-GUCAUCACACUGAAUACCAAU-3' (SEQ ID NO: 1);

ApB-AS:  5'-AUUGGUAUUCAGUGUGAUGACAC-3'
         (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome formulation.
2.1 Reagent preparation.
2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.
2.1.2 Formulation buffer (50 mM citric acid, pH4.0): prepared as described in 2.1.1.
2.1.3 2.1.3 dialysis buffer: 1×phosphate buffer (phosphate-buffered saline, PBS) (Biomics Biotechnologies Co. Ltd).
2.2 preparation of siRNA stock solution.
2.2.1 siRNA dissolvation: ApoB-siRNA stock solution of 50 mg/mL was prepared with solution of 10 mM citrate/30 mM NaCl, pH6.0.
2.2.2 An aliquot of ApoB-siRNA stock solution was diluted in 2000-fold with PBS, measured the concentration of the siRNA. Three parallel measurements were performed for each sample.
2.2.3 Using a UV spectrophotometer, $A_{260}$ value was measured and the actual concentration of ApoB-siRNA in the stock solution was determined. As shown in Table 7, $A_{260}$×50 g/mL per OD×2000/1000=38.51 mg/mL.
2.3 Preparation of lipid storage solution.
2.3.1 Before measurement, the first cationic lipid, the second cationic lipid, phospholipid and long-circulating lipid were pre-equilibrated for about 30 min at room temperature.
2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.
2.4 Preparation of liposome formulation.
2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 26. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 26

The component amounts for F167 formulation
Total volume: 4 mL
Volume of ethanol: 1.2 mL, concentration of ethanol: 30% (v/v)

| Lipid | Concentration (mg/mL) | Amount (mL) |
|---|---|---|
| DLinDMA | 40 | 0.275 |
| DSPC | 20 | 0.176 |
| CL06 | 20 | 0.434 |
| PEG-DMM | 50 | 0.222 |
| Ethanol further added | | 0.093 |

2.4.2 Preparation of siRNA Liposome Formulation.

PFV of desired volume was dispensed in a 50 mL Falcon tubes, pre-equilibrated in a 35° C. water bath for 4-5 min. 52 μL ApoB-siRNA stock solution (38.51 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 μL incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured for its encapsulation efficiency.

2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.
2) The absorbance at 260 nm wavelength was measured using an ultraviolet spectrophotometer (n=3, two parallel measurements were performed for each sample). The results are shown in Table 27.

TABLE 27

A260 value of liposome formulation F167

| Sample | $A_{260}$ value | | $A_{260}$ average | siRNA Con. (mg/mL) |
|---|---|---|---|---|
| Incubation product | 0.3254 | 0.3270 | 0.3204 | 0.4331 |
| | 0.3185 | 0.3225 | | |
| | 0.3123 | 0.3167 | | |
| Sample before chromatography | 0.2345 | 0.2395 | 0.2387 | 0.2420 |
| | 0.2332 | 0.2420 | | |
| | 0.2413 | 0.2418 | | |
| Sample after chromatography | 0.1134 | 0.1095 | 0.1113 | 0.1128 |
| | 0.1107 | 0.1152 | | |
| | 0.1124 | 0.1067 | | |

3) Calculation of the encapsulation efficiency.

As described in Example 10, the actual concentration coefficient was calculated to be 36.87. Based on this coefficient, the actual siRNA concentration of the incubation product, the samples before chromatography, and the samples after chromatography were calculated and presented in Table 27. Based on the concentrations of the siRNA, the encapsulation efficiency was calculated to be 46.6%, and the concentration of ApoB-siRNA was calculated to be 0.293 mg/mL in liposome formulation.

2.4.4 pKa measurement of the PFVs.

As described in Example 10, pKa of the PFVs was measured to be 6.83.

2.4.5 Particle size measurement.

With a Nicomp 370 particle sizing system, the sizes of the pre-formed empty vesicles and the liposome-nucleic acid formulation were determined to be 67.81 nm and 64.75 nm, respectively.

EXAMPLE 25

Function Validation of Liposome Formulations F157, F159, F165 and F167

1. Reagents, Materials, and Instruments 1.1 Reagents and Materials: liposome formulations F157 (Prepared in Example 20), F159 (Prepared in Example 21), F165 (Prepared in Example 22), F167 (Prepared in Example 23), Sodium Chloride solution for injection (Shandong Kangning Pharmaceutical Co.), RISO™ RNA extraction reagent (Biomics Biotechnologies Co. Ltd), EzOmics™ One-Step qPCR kit (Biomics Biotechnologies Co. Ltd), 1 mL sterile syringe (Henan Shuguang Jianshi medical Devices Corporation), Total cholesterol assay kit (Nanjing Jiancheng Corporation).

1.2 Experimental Animals: 4-6 weeks old ICR mice, female, 18-22 g, purchased from Nantong University, Center of Comparative Medicine.

1.3 Instruments: LightCycler 480 Real-Time PCR instrument (Roche, USA), UV-visible spectrophotometer UV759s (Shanghai Jingke Corporation).

2. Experimental Methods 2.1 Experimental groups: According to the body weights measured before the administration of liposome formulation, the mice were divided into five groups, F157 group, F159 group, F165 group, F167 group, and saline group. Administration of the liposome formulation was performed as the follows:

F157 group: the administration amount of F157 formulation was determined according to siRNA dosing of 3 mg/kg;

F159 group: the administration amount of F159 formulation was determined according to siRNA dosing of 3 mg/kg;

F165 group: the administration amount of F165 formulation was determined according to siRNA dosing of 3 mg/kg;

F167 group: the administration amount of F167 formulation was determined according to siRNA dosing of 3 mg/kg;

Saline group: injection of 300 μL of sodium chloride solution.

2.2 Administration of liposome formulation: Mice were fixed by means of a mice fixation device. An administration amount of liposome formulation was calculated according to siRNA dosing of 3 mg/kg. Using a 1 mL sterile syringe, the determined amount of liposome formulation was injected into mice, through the tail vein. The control group was injected with 300 μL of sodium chloride solution.

2.3 Measurement of serum total cholesterol levels of the mice 48 h after administration of liposome formulation, body weights of the mice were determined. By means of removal of an eye ball, about 800 μL of blood was obtained from each mouse. After incubated at 4° C. for one hour, the blood was centrifuged at 3000 rpm for 10 min, to isolate mouse serum. 10 μL of the serum was taken for total cholesterol measurement, according to the manufacture's instruction to measure the absorbance at 500 nm.

The content of cholesterol is calculated as: the content of cholesterol=($A_{500}$ value of the sample/$A_{500}$ value of the standard)×concentration of the standard (concentration of the standard: 200 mg/dL, 5.17 mM).

2.4 Measurement of ApoB mRNA level in mice liver using Real-time quantitative PCR.

48 h after administration of lipid-siRNA formulation, the mice were sacrificed. Three tissue samples were collected from different locations of mice liver. Total RNAs were extracted using RISO™ RNA kit, according to manufacturer's instruction. The mRNA expressional levels of ApoB gene were determined, using qRT-PCR.

Gene-specific primers were used to determine the expressional levels of ApoB gene in tissue sample. A housekeeping gene, GAPDH, was simultaneously amplified and used as an internal reference. For each sample, TF gene and internal reference gene GAPDH were simultaneously amplified, each reaction in triplicate. Gene expressional levels were quantified using One-Step qPCR kit, the reaction system including: 2 μL of RNA template, 12.5 μL of 2×Master Mix, 0.5 μL of 5' end primer (10 μM) and 3' end primer (10 μM) each, 0.5 μL of 50×SYBR Green 1 Solution, RNase-free water was added to make up the system to 25 μL. After mixing, the reaction system was placed on a real-time quantitative PCR instrument to perform the reaction.

Detection of ApoB mRNA: Sequence of the 5' end primer, 5'-AAGCACCTCCGAAAGTACGTG (SEQ ID NO:3); Sequence of the 3' end primer, 5'-CTCCAGCTCTACCT-TACAGTTGA (SEQ ID NO:4). Detection of housekeeping gene GAPDH: Sequence of the 5' end primer, 5'-GTAT-GACTCCACTCACGGCAAA (SEQ ID NO:5); Sequence of the 3' end primer, 5'-GGTCTCGCTCCTGGAAGATG (SEQ ID NO:6). All the primers were synthesized by Biomics Biotechnologies Co. Ltd.

Reaction conditions: reverse transcription at 42° C. for 30 min; pre-denaturation at 95° C. for 5 min; 45 PCR cycles were performed by denaturing at 95° C. for 20 sec, annealing at 58° C. for 30 sec, extension at 72° C. for 30 sec. The dissolution profiles of the reaction were determined as: 95° C./5 min, 58° C./5 min, increased the temperature to 95° C. at a speed of 0.5° C./5 sec.

2.5 Statistic analysis

Statistic analysis was performed using SPSS 14.0 statistical software. Measurement data were presented as x̄±s, the significant differences among multiple groups were tested using single-factor analysis of variance, the significant differences between two groups were tested using t-test, P<0.05 indicates significant difference.

Figure 10:
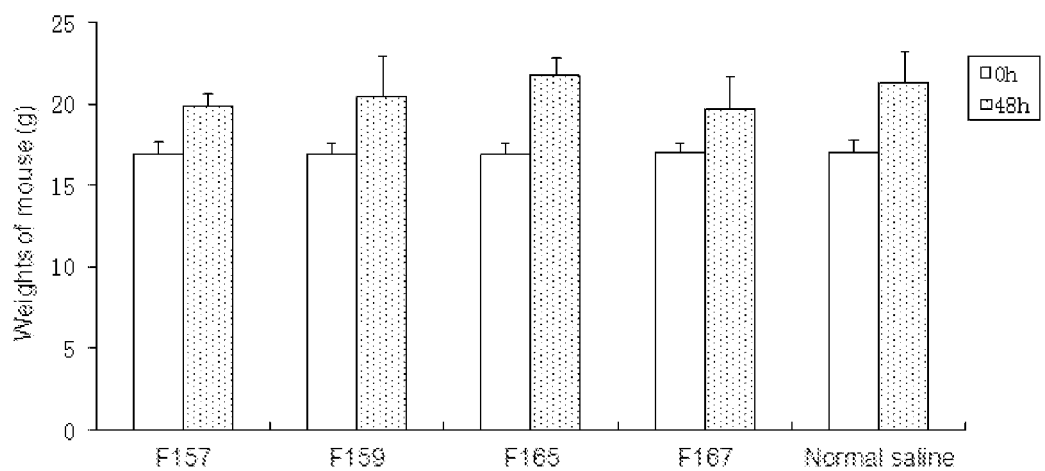
FIG. 10 is a bar graph depicting the body weights of the mice before and after administration of liposome formulations F157, F159, F165 and F167. The horizontal axis represents the experimental groups and the vertical axis represents the body weights of the mice.

3. Experimental Results 3.1 The changes of mice body weights. Mice body weights were measured before and after administration of a liposome formulation. The changes of mice body weights can be used as an indirect index for the toxicity of the liposome formulation. As shown in FIG. 10, no significant change of mice body weights was observed in each group, before and after administration of the liposome formulation. This indicated no significant toxicity of the liposome formulation in concerned.

Figure 11:
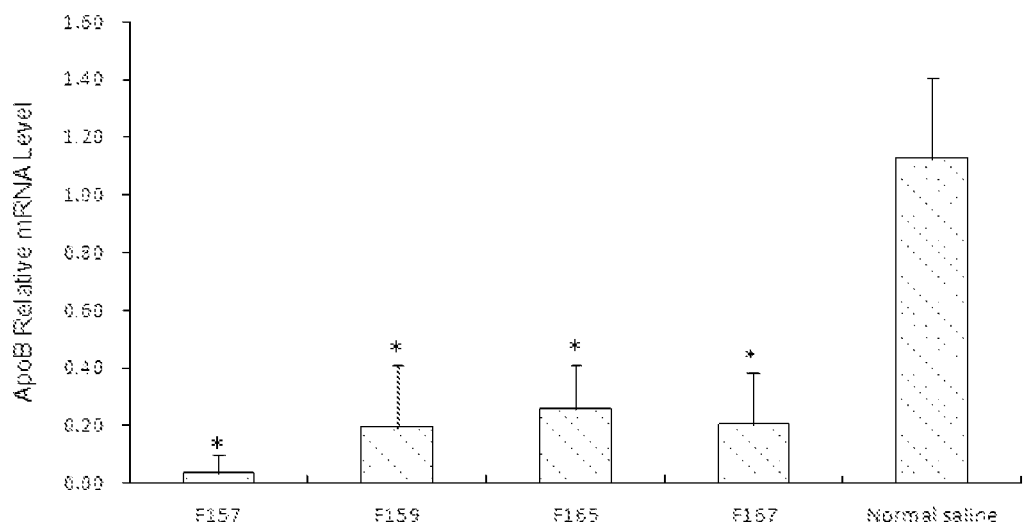
FIG. 11 is a bar graph depicting the relatively expressional levels of ApoB mRNA in mice liver after administration of liposome formulations F157, F159, F165 and F167. The horizontal axis represents the experimental groups and the vertical axis represents the relatively expressional levels of ApoB mRNA in mice liver.

3.2 The changes of mRNA level of ApoB were shown in FIG. 11. Administration of liposome formulations F157, F159, F165 and F167 effectively inhibited the expression of ApoB mRNA in the liver (*P<0.05).

In summary, therapeutic nucleic acids, for example siRNAs, were successfully delivered to target tissues or organs by liposome formulations F157, F159, F165 and F167, and therapeutic nucleic acid can efficiently exhibit their functions.

EXAMPLE 26

Preparation of Liposome Formulation F155
1. Reagents, materials, and instruments.
1.1 Reagents.
1.1.1 Lipids: the first cationic lipid, CL01, prepared in Example 5: the second cationic lipid, CL08, prepared in Example 7; phospholipids, DSPC, purchased from Shanghai Advanced Vehicle Technology Corporation; long-circulating lipid, PEG-cDMA, prepared in Example 9.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

```
ApB-S:   5'-GUCAUCACACUGAAUACCAAU-3' (SEQ ID NO: 1);

ApB-AS:  5'-AUUGGUAUUCAGUGUGAUGACAC-3'
         (SEQ ID NO: 2).
```

1.3 Materials: ion exchange column, Vivapure 1) Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation.
2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.
2.1.2 Formulation buffer (50 mM citric acid, pH4.0): prepared as described in 2.1.1.
2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolution: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, for measuring the concentration of the siRNA. Three parallel measurements were performed for each sample.

2.2.3 Using a UV spectrophotometer, $A_{260}$ value was measured and the actual concentration of ApoB-siRNA in the stock solution was determined as: $A_{260} \times 50$ g/mL per OD×2000/1000=64.62 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were solubilized in absolute ethanol at a molar ratio of 40:40:10:10, respectively. The amounts of the lipid are listed in Table 28. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 28

The component amounts for F155 formulation
Total volume: 3.0 mL
Volume of ethanol: 0.9 mL, concentration of ethanol: 30% (v/v)

| Lipid | Concentration (mg/mL) | Amount (mL) |
|---|---|---|
| CL-01 | 40 | 0.087 |
| DSPC | 20 | 0.108 |
| CL06 | 20 | 0.387 |
| PEG-c-DMA | 50 | 0.139 |
| Ethanol further added | | 0.179 |

2.4.2 Preparation of liposome formulation.

PFV of desired volume was dispensed in a 50 mL Falcon tubes, pre-equilibrated in a 35° C. water bath for 4-5 min. 19.7 μL ApoB-siRNA stock solution (64.62 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 6004 incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured for its encapsulation efficiency. 2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 29.

TABLE 29

A260 value of liposome formulation F155

| Sample | $A_{260}$ value | $A_{260}$ average | siRNA Con. (mg/mL) |
|---|---|---|---|
| Incubation product | 0.2018 0.2092 | 0.1973 | 0.3589 |
| | 0.1902 0.1923 | | |
| | 0.1911 0.1992 | | |
| Sample before chromatography | 0.1471 0.1493 | 0.1514 | 0.2065 |
| | 0.1527 0.1551 | | |
| | 0.1519 0.1523 | | |
| Sample after chromatography | 0.1221 0.1202 | 0.1226 | 0.1672 |
| | 0.1241 0.1196 | | |
| | 0.1282 0.1212 | | |

3) Calculation of the encapsulation efficiency.

As described in Example 10, the actual concentration coefficient was calculated to be 49.61. Based on this coefficient, the actual siRNA concentration of the incubation product, the samples before chromatography, and the samples after chromatography were calculated and presented in Table 29. Based on the concentrations of the siRNA, the encapsulation efficiency was calculated to be 80.9%, and the concentration of ApoB-siRNA was calculated to be 0.167 mg/mL in liposome formulation.

2.4.4 pKa measurement of the PFVs.

As described in Example 10, pKa of the PFVs was measured to be 5.89.

2.4.5 Particle size measurement.

With a Nicomp 370 particle sizing system, the sizes of the pre-formed empty vesicles and the liposome formulation were determined to be 60.07 nm and 63.63 nm, respectively.

EXAMPLE 27

Preparation of Liposome Formulation F156

1. Reagents, materials, and instruments.

1.1 Reagents.

1.1.1 Lipids: the first cationic lipid, CL01, prepared in Example 5; the second cationic lipid, CL08, prepared in Example 7; phospholipids, DSPC, purchased from Shanghai Advanced Vehicle Technology Corporation; long-circulating lipid, PEG-c-DMA, prepared in Example 9.

1.1.2 TNS was purchased from Sigma-Aldrich Corporation; other biochemical reagents are domestic or imported products with analytical purity, including anhydrous ethanol, methanol, chloroform, citric acid, sodium citrate, NaCl, etc.

1.2 ApoB-siRNA, synthesized by Biomics Biotechnologies Co. Ltd and provided as a freeze-dried powder. Sequences of the siRNA are:

ApB-S:  5'-GUCAUCACACUGAAUACCAAU-3' (SEQ ID NO: 1);

ApB-AS: 5'-AUUGGUAUUCAGUGUGAUGACAC-3'
        (SEQ ID NO: 2).

1.3 Materials: ion exchange column, Vivapure D Mini H (Sartorius Stedim Corporation, USA); Ultracel-100 centrifugal ultrafiltration (Millipore Corporation, USA); dialysis membrane, Nuclepore Membrane Circles (80 nm) (Whatman Corporation, USA); dialysis bags and syringe-type filters were purchased from Sangon Corporation; dialysis bags MD24 (MW: 20000, Shanghai BaoMan BioChem Corporation); syringe-type filters (Shanghai Sangon Corporation); 50 mL Falcon tube (Corning Corporation, USA).

1.4 Instruments: Vortex-shaker (VWR Corporation, USA); thermostatic water bath (Jiangsu Tianhong Corporation); centrifuge (Eppendorf Corporation, USA); UV-visible spectrophotometer (Shanghai Jingke Corporation); magnetic stirrer (Shanghai Meiying-Pu Instrument); NLI liposome extruder (ATS Corporation, Canada), clean Benches (Suzhou Purification Equipment Corporation); high-speed refrigerated centrifuge (Xiangyi Corporation), fluorescence spectrophotometer (RF-5301PC, Shimadzu Corporation).

2. Preparation of Liposome Formulation 2.1 Reagent preparation.

2.1.1 siRNA dissolving buffer (10 mM citric acid, 30 mM NaCl, pH6.0): prepared with RNase-free water or water for injection, upon adjusting pH, filtered with 0.22 μm membrane filter. Aliquots were stored at −20° C.

2.12 Formulation buffer (50 mM citric acid, pH4.0): prepared as described in 2.1.1.

2.1.3 Dialysis buffer: 1×phosphate buffer (phosphate-buffered saline, PBS) (Biomics Biotechnologies Co. Ltd).

2.2 Preparation of siRNA stock solution.

2.2.1 siRNA dissolvation: ApoB-siRNA stock solution of 50 mg/mL was prepared with solution of 10 mM citrate/30 mM NaCl, pH6.0.

2.2.2 An aliquot of ApoB-siRNA stock solution was diluted in 2000-fold with PBS, for measuring the concentration of the siRNA. Three parallel measurements were performed for each sample.

2.2.3 Using a UV spectrophotometer, $A_2 60$ value was measured and the actual concentration of ApoB-siRNA in the stock solution was determined as: $A_{260} \times 50$ g/mL per OD×2000/1000=64.62 mg/mL.

2.3 Preparation of lipid storage solution.

2.3.1 Before measurement, the first cationic lipid, the second cationic lipid, phospholipid and long-circulating lipid were pre-equilibrated for about 30 min at room temperature.

2.3.2 Stock solution of the first cationic lipid (40 mg/mL) was prepared with 100% ethanol. Stock solution of the second cationic lipid (20 mg/mL) was prepared with 100% ethanol. Stock solution of DSPC (20 mg/mL) was prepared with 100% ethanol. Stock solution of long-circulating lipid (50 mg/mL) was prepared with 100% ethanol.

2.4 Preparation of liposome formulation.

2.4.1 Preparation of pre-formed vesicles (PFV).

The first cationic lipid, the second cationic lipid, the phospholipid, and the long-circulating lipid were dissolved in absolute ethanol at a molar ratio of 40:40:10:10, respectively. The amounts of the lipid are listed in Table 30. After all the lipids were completely dissolved, the obtained ethanol solution of lipid mixture was added into a formulation buffer under stirring, to achieve a final ethanol concentration of 30% (v/v). Under a pressure of 200 psi, the lipids were extruded through two stacked Nuclepore Membrane Circles at room temperature, using a NLI liposome extruder. These procedures resulted in uniform PFV particles, whose sizes were determined using a particle sizing system.

TABLE 30

The component amounts for F156 formulation
Total volume: 3.0 mL
Volume of ethanol: 0.9 mL, concentration of ethanol: 30% (v/v)

| Lipid | Concentration (mg/mL) | Amount (mL) |
|---|---|---|
| CL-01 | 40 | 0.325 |
| DSPC | 20 | 0.134 |
| CL08 | 20 | 0.160 |
| PEG-c-DMA | 50 | 0.172 |
| Ethanol further added | | 0.109 |

2.4.2 Preparation of liposome formulation.

PFV of desired volume was dispensed in a 50 mL Falcon tubes, pre-equilibrated in a 35° C. water bath for 4-5 min. 24.5 μL ApoB-siRNA stock solution (64.62 mg/mL) was formulated into 0.8 mL of siRNA/formulation buffer/ethanol solution, to ensure ethanol volume of 30%. The siRNA/formulation buffer/ethanol solution was added slowly to the PFV solution, incubated at 35° C. for 30 min. After incubation, 600 μL incubation product was used for $A_{260}$ measurement. The resulted liposome formulation was dialyzed overnight in 1×PBS, using a MD24 dialysis bag. The dialyzed product was then recovered, filtered sterilization using a 0.2 μm syringe filter. 600 μL of the product was measured for its encapsulation efficiency.

2.4.3 Measurement of encapsulation efficiency.

300 μL steriled product flew through Vivapure D Mini H (ion exchange column), according to the manufacturer's instructions, so as to perform a separation procedure. The resulted product was the sample after chromatography. The remaining original sample of 300 μL was the sample before chromatography.

1) According to Table 3, the samples for OD measurement ($A_{260}$) were prepared.

2) The absorbance at 260 nm wavelength was determined, using an ultraviolet spectrophotometer (n=3, two parallel measurements were performed for each sample). The results are shown in Table 31.

TABLE 31

A260 value of liposome formulation F156

| Sample | $A_{260}$ value | | $A_{260}$ average | siRNA Con. (mg/mL) |
|---|---|---|---|---|
| Incubation product | 0.2305 | 0.2378 | 0.2347 | 0.4486 |
|  | 0.2351 | 0.2367 | | |
|  | 0.2332 | 0.2348 | | |
| Sample before chromatography | 0.1722 | 0.1732 | 0.1753 | 0.2514 |
|  | 0.1780 | 0.1748 | | |
|  | 0.1784 | 0.1754 | | |

TABLE 31-continued

A260 value of liposome formulation F156

| Sample | $A_{260}$ value | | $A_{260}$ average | siRNA Con. (mg/mL) |
|---|---|---|---|---|
| Sample after chromatography | 0.0524 0.0489 0.0491 | 0.0570 0.0474 0.0501 | 0.0508 | 0.0729 |

3) Calculation of the encapsulation efficiency.

As described in Example 10, the actual concentration coefficient was calculated to be 52.13. Based on this coefficient, the actual siRNA concentration of the incubation product, the samples before chromatography, and the samples after chromatography were calculated and presented in Table 31. Based on the concentrations of the siRNA, the encapsulation efficiency was calculated to be 29%, and the concentration of ApoB-siRNA was calculated to be 0.073 mg/mL in liposome formulation.

2.4.4 pKa measurement of the PFVs.

As described in Example 10, pKa of the PFVs was measured to be 6.33.

2.4.5 Particle size measurement.

With a Nicomp 370 particle sizing system, the sizes of the pre-formed empty vesicles and the liposome formulation were determined to be 82.88 nm and 69.70 nm, respectively.

EXAMPLE 28

Function Validation of Liposome Formulations F155 and F156

1. Reagents, Materials, and Instruments.

1.1 Reagents and Materials: liposome formulations F155 (Prepared in Example 25) and F156 (Prepared in Example 26), Sodium Chloride solution for injection (Shandong Kangning Pharmaceutical Co.), RISO™ RNA RNA extraction reagent (Biomics Biotechnologies Co. Ltd), EzOmics™ One-Step qPCR kit (Biomics Biotechnologies Co. Ltd), 1 mL sterile syringe (Henan Shuguang Jianshi medical Devices Corporation), Total cholesterol assay kit (Nanjing Jiancheng Corporation).

1.2 Experimental Animals: 4-6 weeks old ICR mice, female, 18-22 g, purchased from Nantong University, Center of Comparative Medicine.

1.3 Instruments: LightCycler 480 Real-Time PCR instrument (Roche, USA), UV-visible spectrophotometer UV 759s (Shanghai Jingke Corporation).

2. Experimental Methods 2.1 Experimental groups: According to the body weights measured before the administration of liposome formulation, the mice were divided into three groups, F155 group, F156 group, and saline group. Administration of the liposome formulation was performed as the follows:

F155 group: the administration amount of F155 formulation was determined according to siRNA dosing of 1 mg/kg;

F156 group: the administration amount of F156 formulation was determined according to siRNA dosing of 1 mg/kg;

Saline group: injection of 300 μL of sodium chloride solution.

2.2 Administration of liposome formulation: Mice were fixed by means of a mice fixation device. An administration amount of liposome formulation was calculated according to siRNA dosing of 1 mg/kg. Using a 1 mL sterile syringe, the determined amount of liposome formulation was injected into mice, through the tail vein. The control group was injected with 300 μL of sodium chloride solution.

2.3 Measurement of serum total cholesterol levels of the mice 48 h after administration of lipid-siRNA formulation, body weights of the mice were determined. By means of removal of an eye ball, about 800 μL of blood was obtained from each mouse. After incubated at 4° C. for one hour, the blood was centrifuged at 3000 rpm for 10 min, to isolate mouse serum. 10 μL of the serum was taken for total cholesterol measurement, according to the manufacture's instruction to measure absorbance at 500 nm.

The content of cholesterol is calculated as: the content of cholesterol=($A_{500}$ value of the sample/$A_{500}$ value of the standard)×concentration of the standard (concentration of the standard: 200 mg/dL, 5.17 mM).

2.4 Measurement of ApoB mRNA level in mice liver using Real-time quantitative PCR.

48 h after administration of lipid-siRNA formulation, the mice were sacrificed. Three tissue samples were collected from different locations of mice liver. Total RNAs were extracted using RISO™ RNA kit, according to manufacturer's instruction. The mRNA expressional levels of ApoB gene in mice liver were determined, using qRT-PCR.

Gene-specific primers were used to determine the mRNA expressional levels of ApoB gene in tissue sample. A housekeeping gene, GAPDH, was simultaneously amplified and used as an internal reference. For each sample, TF gene and internal reference gene GAPDH were simultaneously amplified, each reaction in triplicate. Gene expressional levels were quantified using One-Step qPCR kit, the reaction system including: 2 μL of RNA template, 12.5 μL of 2×Master Mix, 0.5 μL of 5' end primer (10 μM) and 3' end primer (10 μM) each, 0.5 μL of 50×SYBR Green I Solution, RNase-free water was added to make up the system to 25 μL. After mixing, the reaction system was placed on a real-time quantitative PCR instrument to perform the reaction.

Detection of ApoB mRNA: Sequence of the 5' end primer, 5'-AAGCACCTCCGAAAGTACGTG (SEQ ID NO:3); Sequence of the 3' end primer, 5'-CTCCAGCTCTACCT-TACAGTTGA (SEQ ID NO:4). Detection of housekeeping gene GAPDH: Sequence of the 5' end primer, 5'-GTAT-GACTCCACTCACGGCAAA (SEQ ID NO:5); Sequence of the 3' end primer, 5'-GGTCTCGCTCCTGGAAGATG (SEQ ID NO:6). All the primers were synthesized by Biomics Biotechnologies Co. Ltd.

Reaction conditions: reverse transcription at 42° C. for 30 min; pre-denaturation at 95° C. for 5 min; 45 PCR cycles were performed by denaturing at 95° C. for 20 sec, annealing at 58° C. for 30 sec, extensing at 72° C. for 30 sec. The dissolution profiles of the reaction were determined as: 95° C./5 min, 58° C./5 min, increased the temperature to 95° C. at a speed of 0.5° C./5 sec.

2.5 Statistic Analysis

Statistic analysis was performed using SPSS 14.0 statistical software. Measurement data were presented as the significant differences among multiple groups were tested using single-factor analysis of variance, the significant differences between two groups were tested using t-test, $P<0.05$ indicates significant difference.

Figure 12:
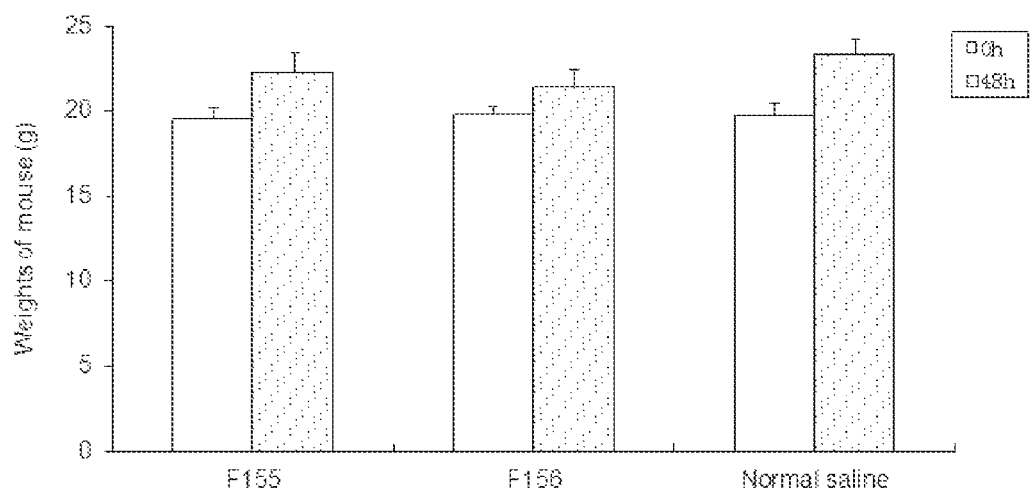
FIG. 12 is a bar graph depicting the body weights of the mice before and after administration of liposome formulations F155 and F156. The horizontal axis represents the experimental groups and the vertical axis represents the body weights of the mice.

3. Experimental Results 3.1 The changes of mice body weights. Mice body weights were measured before and after administration of a liposome formulation. The changes of mice body weights can be used as an indirect index for the toxicity of the liposome formulation. As shown in FIG. 12, no significant change of mice body weights was observed in each group, before and after administration of the lipid-siRNA formulation. This indicated no significant toxicity of the liposome formulation in concerned.

Figure 13:
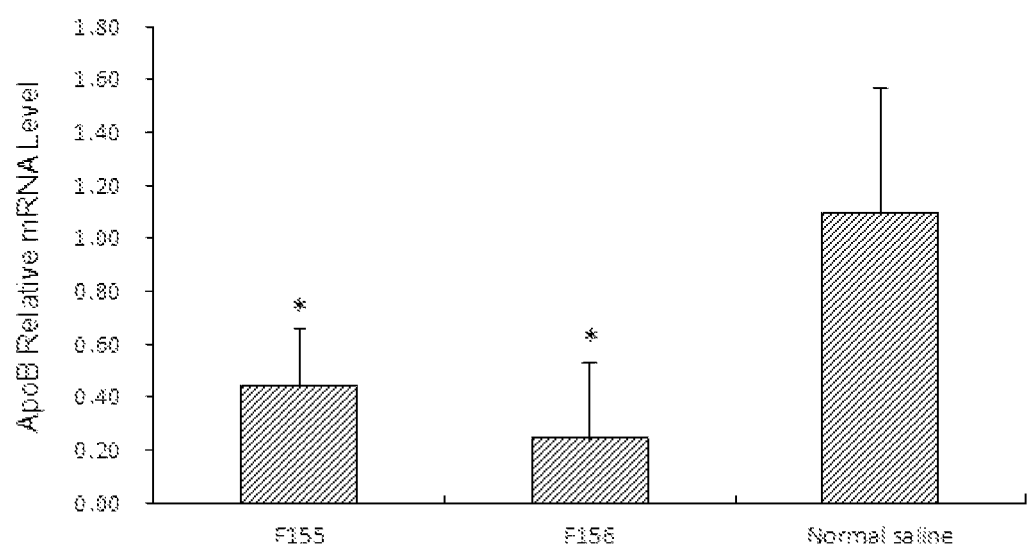
FIG. 13 is a bar graph depicting the relatively expressional levels of ApoB mRNA in mice liver after administration of liposome formulations F155 and F156. The horizontal axis represents the experimental groups and the vertical axis represents the relatively expressional levels of ApoB mRNA in mice liver.

3.2 The changes of mRNA level of ApoB were shown in FIG. 13. Administration of liposome formulations F155 and F156 effectively inhibited the expression of ApoB mRNA in the liver (*P<0.05).

In summary, therapeutic nucleic acids, for example siRNAs, were successfully delivered to target tissues or organs by liposome formulations F155 and F156, and therapeutic nucleic acids can efficiently exhibit their functions.

The liposome formulation provided in the present invention is a therapeutic formulation for in vivo delivery of agents, which may be used to encapsulate drugs and delivery them to target tissues in vivo. When the liposome formulations were further formulated with nucleic acid drugs, the resulted formulations will have a therapeutic effect in disease treatment. Liposome-nucleic acid formulations can be administered in a variety of ways, e.g. by intravenous, parenteral, or intraperitoneal administered. Shown by the above embodiments, the present invention provides a liposome formulation, by which therapeutic nucleic acids can be delivered into cells, such as the cells in lung, liver, or other inflammatory target tissues. Liposome-nucleic acid formulations may be also used to treat diseases in mammals. The liposome formulation provided in the present invention comprises pairs of complementary cationic lipid, phospholipids and long-circulating lipid phospholipids, the liposome formulation may deliver nucleic acid drugs to therapeutic target tissues, to treat diseases caused by the expression or over-expression of a gene or genes.

The liposome formulation provided in the present invention may be a liquid, such as in an emulsion drop, emulsions or aerosol form. The liposome formulation may be a solid substance, which can be dissolved into a liquid prior to administration; such a solid substance may be administrated as a powder, or in the form of a capsule, tablet or gel.

What is claimed is:

1. A liposome formulation comprising complementary cationic lipid pairs, phospholipids, and long-circulating lipids, wherein:
   a. the complementary cationic lipid pairs comprise first cationic lipids and second cationic lipids wherein the first cationic lipids comprise heptatriaconta-6,9,28,31-tetraen-19-yl-4-(dimethylamino)butanoate or N,N-dimethyl-2,3-dilinoleyloxypropylamine and the second cationic lipids comprise cholesteryl 3-(dimethylamino)propanoate or cholesteryl 2-(dimethylamino)acetate;
   b. the phospholipids comprise distearoyl phosphatidyl choline; and
   c. the long-circulating lipids comprise N-[(methoxy poly(ethylene glycol)2000)carbamoyl]-1,2-dimyristyloxy-propyl-3-amine (PEG-c-DMA), heptatriaconta-6,9,28,31-tetra-en-19-ol methoxy poly(ethylene glycol)2000 carbamate (PEG-DLM), cholesterol methoxy poly(ethylene glycol)2000 carbamate (PEG-Chol), or nonacosan-15-ol methoxy poly(ethylene glycol)2000 carbamate (PEG-DMM).

2. The liposome formulation of claim 1, wherein the liposome formulation comprises 20~80% of the complementary cationic lipid pairs, 10% of the phospholipids, and 10% of the long-circulating lipids, on a molar basis.

3. The liposome formulation of claim 1, wherein the respective molar percentages of the first cationic lipids and the second cationic lipids are 20~60% in the formulation.

4. The liposome formulation of claim 1, further comprising a therapeutic agent.

5. The liposome formulation of claim 4, wherein the therapeutic agent is a nucleic acid.

6. The liposome formulation of claim 1 wherein the first cationic lipids comprise N,N-dimethyl-2,3-dilinoleyloxypropylamine.

7. A method of preparing the liposome formulation of claim 1, comprising mixing the complementary cationic lipid pairs with the phospholipid and the long-circulating lipid to generate pre-formed vesicles; and then mixing the pre-formed vesicles with a nucleic acid solution to generate a liposome-nucleic acid formulation.

8. A method of treating a disease caused by abnormal gene expression comprising administering the liposome formulation of claim 6 to a patient having said abnormal gene expression.

9. The liposome formulation of claim 5, wherein the nucleic acid comprises an siRNA, an miRNA, a small ligand RNA, an RNA aptamer, or combinations thereof.

10. The liposome formulation of claim 1 wherein the first cationic lipids comprise heptatriaconta-6,9,28,31-tetraen-19-yl-4-(dimethylamino)butanoate.

11. The liposome formulation of claim 1 wherein the second cationic lipids comprise cholesteryl 3-(dimethylamino)propanoate.

12. The liposome formulation of claim 1 wherein the second cationic lipids comprise cholesteryl 2-(dimethylamino)acetate.

13. The liposome formulation of claim 1 wherein the long-circulating lipids comprise PEG-c-DMA.

14. The liposome formulation of claim 1 wherein the long-circulating lipids comprise PEG-DLM.

15. The liposome formulation of claim 1 wherein the long-circulating lipids comprise PEG-Chol.

16. The liposome formulation of claim 1 wherein the long-circulating lipids comprise PEG-DMM.

17. The liposome formulation of claim 1 wherein:
   a) the first cationic lipids comprise heptatriaconta-6,9,28,31-tetraen-19-yl-4-(dimethylamino)butanoate;
   b) the second cationic lipids comprise cholesteryl 3-(dimethylamino)propanoate or cholesteryl 2-(dimethylamino)acetate;
   c) the phospholipids comprise distearoyl phosphatidyl choline; and
   d) the long-circulating lipids comprise PEG-c-DMA.

* * * * *